US012692465B2

(12) United States Patent
Wang

(10) Patent No.: US 12,692,465 B2
(45) Date of Patent: Jul. 28, 2026

(54) NUCLEIC ACID EXTRACTION MICROFLUIDIC CHIP, AND NUCLEIC ACID EXTRACTION DEVICE AND EXTRACTION METHOD

(71) Applicant: BOE Technology Group Co., Ltd., Beijing (CN)

(72) Inventor: Jiapeng Wang, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 1310 days.

(21) Appl. No.: 17/417,850

(22) PCT Filed: Sep. 22, 2020

(86) PCT No.: PCT/CN2020/116853
§ 371 (c)(1),
(2) Date: Jun. 24, 2021

(87) PCT Pub. No.: WO2022/061521
PCT Pub. Date: Mar. 31, 2022

(65) Prior Publication Data
US 2022/0333048 A1     Oct. 20, 2022

(51) Int. Cl.
*C12M 1/00*          (2006.01)
*B01L 3/00*          (2006.01)
(Continued)

(52) U.S. Cl.
CPC ......... *C12M 1/00* (2013.01); *B01L 3/502715* (2013.01); *C12N 15/1013* (2013.01);
(Continued)

(58) Field of Classification Search
None
See application file for complete search history.

(56) References Cited

U.S. PATENT DOCUMENTS

2003/0057391 A1    3/2003  Krulevitch et al.
2007/0051412 A1*   3/2007  Heath ................. F16K 99/0059
                                                   216/2
(Continued)

FOREIGN PATENT DOCUMENTS

CN        102679039 A      9/2012
CN        102735864 A     10/2012
(Continued)

OTHER PUBLICATIONS

Hess et al., "Review on pneumatic operations in centrifugal microfluidics", vol. 19, No. 22, Sep. 2019, pp. 3745-3770.
(Continued)

*Primary Examiner* — Michael A Marcheschi
*Assistant Examiner* — Nathan G Esperon
(74) *Attorney, Agent, or Firm* — ArentFox Schiff LLP; Michael Fainberg

(57)     ABSTRACT

Embodiments of the disclosure provide a nucleic acid extraction microfluidic chip, and a nucleic acid extraction device and method. The nucleic acid extraction microfluidic chip includes a channel plate including: a mixed lysis zone, an extraction zone adjacent to the mixed lysis zone, a gas-pressure driven port in communication with an exterior, a first type of channel communicating the mixed lysis zone with the extraction zone, and a second type of channel communicating the extraction zone with the gas-pressure driven port; a cover plate opposite to the channel plate, wherein the cover plate includes a sample inlet and a liquid inlet through hole in a location corresponding to the mixed lysis zone; and a solution accommodating cavity, on a side of the cover plate away from the channel plate, wherein the solution accommodating cavity communicates with the mixed lysis zone of the channel plate through the liquid inlet through hole.

8 Claims, 15 Drawing Sheets

(51) Int. Cl.
    *C12N 15/10*         (2006.01)
    *C12Q 1/68*         (2018.01)

(52) U.S. Cl.
    CPC ............ *C12Q 1/68* (2013.01); *B01L 2200/10*
    (2013.01); *C12N 2310/00* (2013.01); *C12N*
    *2310/10* (2013.01); *C12Q 2560/00* (2013.01);
    *C12Q 2561/00* (2013.01)

(56)         References Cited

U.S. PATENT DOCUMENTS

| | | | |
|---|---|---|---|
| 2008/0227185 A1 | 9/2008 | Schonfeld et al. | |
| 2009/0035847 A1 | 2/2009 | Cho et al. | |
| 2010/0112667 A1* | 5/2010 | Sundaram .......... | C12N 15/1006 |
| | | | 435/235.1 |
| 2011/0005932 A1* | 1/2011 | Jovanovich .......... | C12Q 1/6806 |
| | | | 204/453 |
| 2012/0115738 A1* | 5/2012 | Zhou ........................ | B01F 33/30 |
| | | | 435/6.12 |
| 2012/0138833 A1 | 6/2012 | Matteo | |
| 2016/0346780 A1 | 12/2016 | Bransky et al. | |
| 2017/0058324 A1* | 3/2017 | Balog ............... | B01L 3/502738 |
| 2017/0080422 A1* | 3/2017 | Maaskant .......... | B01D 17/0217 |
| 2021/0031183 A1* | 2/2021 | Wernerehl ................ | B01L 7/52 |
| 2021/0039103 A1 | 2/2021 | Takata et al. | |
| 2023/0028621 A1* | 1/2023 | Tiirola ............... | C12N 15/1017 |

FOREIGN PATENT DOCUMENTS

| | | | |
|---|---|---|---|
| CN | 103335154 A | 10/2013 | |
| CN | 203925955 U | 11/2014 | |
| CN | 105536898 A | 5/2016 | |
| CN | 205687904 U | 11/2016 | |
| CN | 106660058 A | 5/2017 | |
| CN | 206637105 U | 11/2017 | |
| CN | 107615068 A | 1/2018 | |
| CN | 108841818 A | 11/2018 | |
| CN | 109536366 | * | 3/2019 |
| CN | 109536366 A | | 3/2019 |
| CN | 110257245 A | 9/2019 | |
| CN | 110343611 A | 10/2019 | |
| CN | 110656108 A | 1/2020 | |
| CN | 111057638 A | 4/2020 | |
| CN | 210656872 U | 6/2020 | |
| CN | 111592971 A | 8/2020 | |
| CN | 115400806 A | 11/2022 | |
| CN | 115703993 A | 2/2023 | |
| WO | 2023/020220 A1 | 2/2023 | |

OTHER PUBLICATIONS

Office Action received for Chinese Patent Application No. 202080002055.X, mailed on Apr. 24, 2024, 34 pages (19 pages of English Translation and 15 pages of Original Document).
Office Action received for Chinese Patent Application No. 202080002055.X, mailed on May 23, 2024, 25 pages (15 pages of English Translation and 10 pages of Original Document).
Yuqin et al., Application of Magnetic Control Technique in Microfluidic Chips, vol. 22, No. 1, Jan. 2010, 7 pages (English Abstract Submitted).
Notice of Allowance received for Chinese Patent Application No. 202080002055.X, mailed on Mar. 7, 2025, 6 pages (2 pages of English Translation and 4 pages of Original Document).

* cited by examiner

1

NUCLEIC ACID EXTRACTION MICROFLUIDIC CHIP, AND NUCLEIC ACID EXTRACTION DEVICE AND EXTRACTION METHOD

The present disclosure is a National Stage of International Application No. PCT/CN2020/116853, filed on Sep. 22, 2020, the content of which is incorporated herein by reference in its entirety.

FIELD

The present disclosure relates to the field of microfluidic technology, in particular to a nucleic acid extraction microfluidic chip, and a nucleic acid extraction device and extraction method.

BACKGROUND

Isolation and purification techniques of a biological macromolecule from a nucleic acid are the most central basis in the sample preparation process for molecular detection, and key techniques in the life science research and application. Traditional nucleic acid extraction methods mainly employ centrifugal in-tube extraction, wasting space and reagents, and increasing the manufacturing costs. Microfluidic-based nucleic acid extraction methods have been developed as microfluidic technologies have developed. General microfluidic nucleic acid extraction methods are only performed by immobilizing a substance which adsorbs nucleic acid, such as the silica or diatom, on the inner wall of a channel, and then manually introducing the reagent and removing the waste liquid, which are cumbersome in step, time consuming and labor consuming, and poor in result extraction rate and repeatability. In view of this, it is necessary to design and provide a microfluidic chip integrated nucleic acid extraction chip that is efficient and convenient to use.

SUMMARY

An embodiment of the present disclosure provides a nucleic acid extraction microfluidic chip, including:

a channel plate, including: a mixed lysis zone, an extraction zone adjacent to the mixed lysis zone, a gas-pressure driven port in communication with an exterior, a first type of channel communicating the mixed lysis zone with the extraction zone, and a second type of channel communicating the extraction zone with the gas-pressure driven port;

a cover plate, disposed opposite to the channel plate, wherein the cover plate includes a sample inlet and a liquid inlet through hole in a location corresponding to the mixed lysis zone; and a solution accommodating cavity, on a side of the cover plate away from the channel plate, wherein the solution accommodating cavity communicates with the mixed lysis zone of the channel plate through the liquid inlet through hole.

In a possible implementation, the extraction zone includes: an extraction trough with a liquid inlet end and a liquid outlet end;

the mixed lysis zone includes: a mixed lysis groove, as well as a first liquid inlet groove, a second liquid inlet groove and a third liquid inlet groove arranged in sequence in a region where the mixed lysis groove is located;

the first type of channel includes: a first channel communicating the first liquid inlet groove with the liquid inlet end, a second channel communicating the second liquid inlet groove with the liquid inlet end, and a third channel communicating the third liquid inlet groove with the liquid inlet end, wherein the mixed lysis groove is in the second channel;

the second type of channel includes: a fourth channel communicating the liquid outlet end with the gas-pressure driven port; and the liquid inlet through hole includes: a first through hole corresponding to the first liquid inlet groove, a second through hole corresponding to the second liquid inlet groove, and a third through hole corresponding to the third liquid inlet groove.

In a possible implementation, the solution accommodating cavity includes:

a flushing liquid accommodating cavity, in communication with the first liquid inlet groove of the channel plate through the first through hole;

a lysis solution accommodating cavity, in communication with the second liquid inlet groove of the channel plate through the second through hole; and an eluent accommodating cavity, in communication with the third liquid inlet groove of the channel plate through the third through hole.

In a possible implementation, the gas-pressure driven port includes a first gas-pressure driven port and a second gas-pressure driven port, and the fourth channel includes: a first sub-channel communicating the first gas-pressure driven port with the liquid outlet end, and a second sub-channel communicating the second gas-pressure driven port with the liquid outlet end.

In a possible implementation, the channel plate further includes: a sample storage groove at the first sub-channel.

In a possible implementation, the channel plate further includes: a waste liquid storage groove at the second sub-channel.

In a possible implementation, the first channel, the second channel and the third channel converge at a liquid inlet channel to communicate with the liquid inlet end; and the waste liquid storage groove is further in communication with the liquid inlet channel through a fifth channel.

In a possible implementation, the nucleic acid extraction microfluidic chip further includes a magnetic bead positioned within the extraction trough.

In a possible implementation, the nucleic acid extraction microfluidic chip further includes: a magnetic bead accommodating cavity on a side of the cover plate away from the channel plate;

wherein:

the mixed lysis zone further includes: a fourth liquid inlet groove, and a sixth channel communicating the fourth liquid inlet groove with the liquid inlet end;

the cover plate further includes: a fourth through hole corresponding to the fourth liquid inlet groove; and the magnetic bead accommodating cavity is in communication with the fourth liquid inlet groove of the channel plate through the fourth through hole.

In a possible implementation, the first type of channel and the second type of channel are further provided with control valves.

In a possible implementation, the control valves include:

a first control valve in the first channel;

a second control valve in the second channel;

a third control valve in the third channel; and a fourth control valve in the second sub-channel and between the waste liquid storage groove and the liquid outlet end.

In a possible implementation, each of the control valves is a solenoid control valve structure including: an iron block accommodating groove in a surface of the cover plate facing the channel plate, an iron block in the iron block accommodating groove, and an elastic protective membrane sealing the iron block accommodating groove on a side of the iron block facing the channel plate.

In a possible implementation, each of the control valves is a camshaft pressing rod valve structure including: an accommodating rod through slot in a surface of the cover plate away from the channel plate, and an elastic protective membrane on a side of the accommodating rod through slot facing the channel plate.

In a possible implementation, each of the control valves is a gas-pressure driven squeezing valve structure including: a squeezing block accommodating groove in a surface of the cover plate away from the channel plate, a squeezing block in the squeezing block accommodating groove, a bottom membrane on a side of the squeezing block away from the channel plate, and an elastic protective membrane on a side of the squeezing block facing the channel plate; wherein the bottom membrane includes a gas circuit access port communicating with the squeezing block accommodating groove.

In a possible implementation, a protective membrane accommodating groove accommodating the elastic protective membrane is provided in a surface of the cover plate, and an orthographic projection of the protective membrane accommodating groove on the cover plate covers an orthographic projection of the elastic protective membrane on the cover plate.

In a possible implementation, a material of the elastic protective membrane is polydimethylsiloxane.

In a possible implementation, a main body shape of the channel plate is a rectangle, and the channel plate includes a first side edge and a second side edge extending in a first direction, and a third side edge and a fourth side edge extending in a second direction; wherein a shape of the cover plate is the same as a shape of the channel plate;

the channel plate includes a first segment, a second segment and a third segment arranged sequentially in the first direction, and lengths in the second direction of the first segment, the second segment and the third segment decrease sequentially; and the first gas-pressure driven port is at a position, where the first segment protrudes more than the second segment, of the first side edge, and the second gas-pressure driven port is at a position, where the first segment protrudes more than the second segment, of the second side edge.

In a possible implementation, the extraction trough is in the first segment; the mixed lysis groove is in the second segment; and the lysis solution accommodating cavity, the flushing liquid accommodating cavity and the eluent accommodating cavity are in a region where the third segment is located.

In a possible implementation, the extraction trough is of a snake shape.

An embodiment of the present disclosure further provides a nucleic acid extraction device including the nucleic acid extraction microfluidic chip provided by the embodiment of the present disclosure, and the nucleic acid extraction device further includes a magnetic supply component for providing a magnetic bead with a magnetic field.

In a possible implementation, in the condition that each of control valves is a solenoid control valve structure, the nucleic acid extraction device further includes an electromagnet on a side of a channel plate away from the cover plate.

In a possible implementation, in the condition that each of the control valves is a camshaft pressing rod valve structure, the nucleic acid extraction device further includes a camshaft, and a plurality of pressing rods connected to the camshaft.

An embodiment of the present disclosure further provides a nucleic acid extraction method of the nucleic acid extraction device provided by the embodiment of the present disclosure, including:

injecting a sample liquid through the sample inlet into the mixed lysis zone and controlling the solution accommodating cavity to release a lysis solution to lyse the sample liquid by the lysis solution to form a mixed liquid; and applying negative pressure through the gas-pressure driven port to move the mixed liquid into the extraction zone, and performing separation and extraction on the mixed liquid to obtain a nucleic acid by applying negative pressure through a gas-pressure driven port to move the mixed liquid into an extraction zone.

In a possible implementation, the injecting the sample liquid through the sample inlet into the mixed lysis zone and controlling the solution accommodating cavity to release the lysis solution include:

injecting the sample liquid through the sample inlet into a mixed lysis groove, controlling a lysis solution accommodating cavity to release the lysis solution, and moving the lysis solution into the mixed lysis groove to lyse the sample liquid by the lysis solution to form the mixed liquid.

In a possible implementation, a nucleic acid extraction microfluidic chip includes a magnetic bead positioned within an extraction trough; and the applying negative pressure through the gas-pressure driven port to move the mixed liquid into the extraction zone, and the performing separation and extraction on the mixed liquid to obtain the nucleic acid, includes:

applying the negative pressure through the gas-pressure driven port to move the mixed liquid into the extraction trough to mix with the magnetic bead so as to bind the magnetic bead to the nucleic acid formed by the sample liquid lysed;

controlling a flushing liquid accommodating cavity to introduce a flushing liquid into the extraction trough for flushing for a first time period, providing a magnetic field through the magnetic supply component to cause the magnetic bead to be adsorbed to an inner wall of the extraction trough, and discharging liquid that has flushed the magnetic bead through the gas-pressure driven port; and turning off the magnetic field through the magnetic supply component, and controlling the eluent accommodating cavity to introduce an eluent into the extraction trough to separate the nucleic acid from the magnetic bead.

In a possible implementation, a channel plate further includes a sample storage groove; and after controlling the eluent accommodating cavity to introduce the eluent into the extraction trough to separate the nucleic acid from the magnetic bead, the nucleic acid extraction method further includes: moving the nucleic acid into the sample storage groove.

In a possible implementation, the nucleic acid extraction microfluidic chip further includes a waste liquid storage groove; and discharging the liquid that has flushed the magnetic bead through the gas-pressure driven port includes: discharging the liquid that has flushed the magnetic bead through the gas-pressure driven port into the waste liquid storage groove.

In a possible implementation, the gas-pressure driven port includes a first gas-pressure driven port and a second gas-pressure driven port;

moving the lysis solution into the mixed lysis groove includes: sucking the lysis solution into the mixed lysis groove by applying negative pressure to the first gas-pressure driven port;

applying the negative pressure through the gas-pressure driven port to move the mixed liquid into the extraction trough to mix with the magnetic bead includes: applying negative pressure to the first gas-pressure driven port to move the mixed liquid into the extraction trough to mix with the magnetic bead;

discharging the liquid that has flushed the magnetic bead through the gas-pressure driven port includes: sucking the liquid that has flushed the magnetic bead into the waste liquid storage groove by applying negative pressure to the second gas-pressure driven port; and introducing the nucleic acid into the sample storage cavity includes: sucking the nucleic acid into the sample storage groove by applying negative pressure to the first gas-pressure driven port.

In a possible implementation, the nucleic acid extraction microfluidic chip further includes: a first control valve, a second control valve, a third control valve and a fourth control valve;

before the injecting the sample liquid through the sample inlet into the mixed lysis groove, the nucleic acid extraction method further includes: opening the first control valve, the second control valve, the third control valve and the fourth control valve;

before the controlling the flushing liquid accommodating cavity to introduce the flushing liquid into the extraction trough, the nucleic acid extraction method further includes: closing the second control valve;

before the controlling the eluent accommodating cavity to introduce the eluent into the mixed lysis groove, the nucleic acid extraction method further includes: closing the first control valve; and before the moving the nucleic acid into the sample storage groove, the nucleic acid extraction method further includes: closing the fourth control valve.

In a possible implementation, after the moving the mixed liquid into the extraction trough to mix with the magnetic bead and before the controlling the flushing liquid accommodating cavity to introduce the flushing liquid into the extraction trough, the nucleic acid extraction method further includes:

providing a magnetic field through the magnetic supply component to cause the magnetic bead to be adsorbed to an inner wall of a snake-shaped tube, and discharging liquid that has reacted with the lysis solution and not bound to the magnetic bead through the second gas-pressure driven port; and turning off the magnetic field through the magnetic supply component.

DETAILED DESCRIPTION OF THE EMBODIMENTS

In order to make the objectives, technical solutions and advantages of embodiments of the present disclosure clearer, the technical solutions of the embodiments of the present disclosure will be clearly and completely described below in conjunction with the accompanying drawings of the embodiments of the present disclosure. Apparently, the described embodiments are some, but not all, embodiments of the present disclosure. Based on the described embodiments of the present disclosure, all other embodiments obtained by a person of ordinary skill in the art without inventive effort fall within the scope of protection of the present disclosure.

Unless otherwise defined, technical or scientific terms used herein are to be taken as commonly understood by one of ordinary skill in the art to which this disclosure belongs. The terms "first", "second", and the like, as used in this disclosure, do not denote any order, quantity, or importance, but are merely used to distinguish one component from another. The word "including" or "containing" and the like means that elements or items preceding the word appear to encompass elements or items listed after the word and equivalents thereof, but not to the exclusion of other elements or items. "Connect" or "connected" and the like are not restricted to physical or mechanical connections, but can include electrical connections, whether direct or indirect. "Up", "down", "left", "right" etc. are only used to indicate relative positional relationships, which may change accordingly when the absolute position of the object being described changes.

To keep the following description of the embodiments of the present disclosure clear and concise, the present disclosure omits detailed descriptions of known functions and known components.

Figure 1:
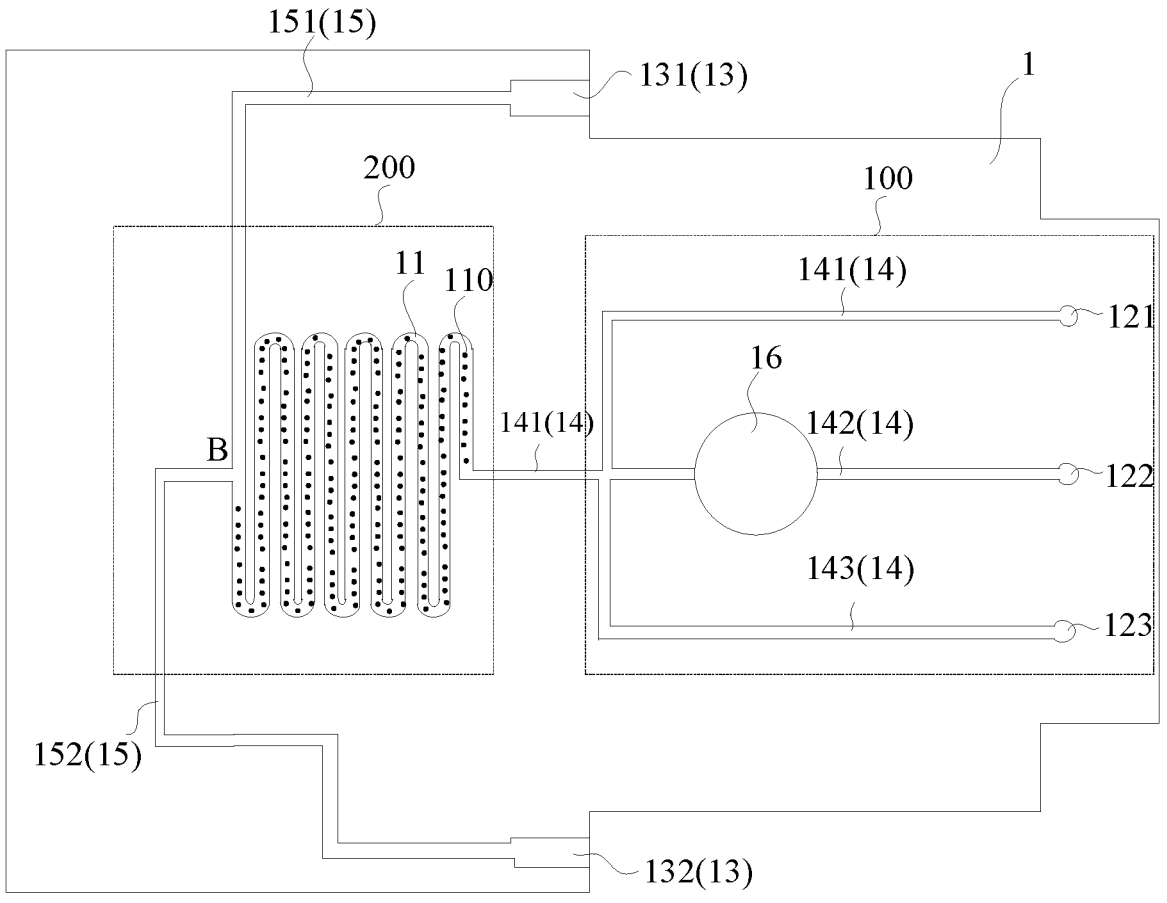
FIG. 1 is a schematic structural diagram of a channel plate according to embodiments of the present disclosure.
Figure 2:
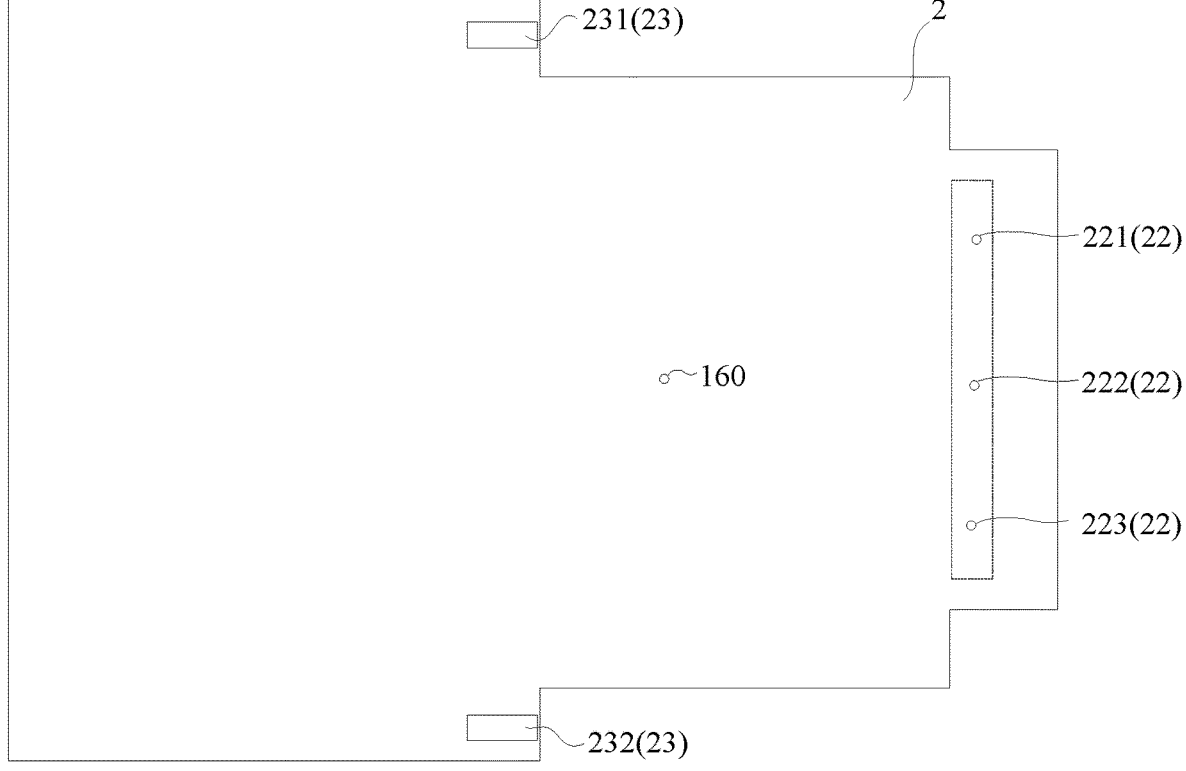
FIG. 2 is a schematic structural diagram of a cover plate according to embodiments of the present disclosure.
Figure 3:
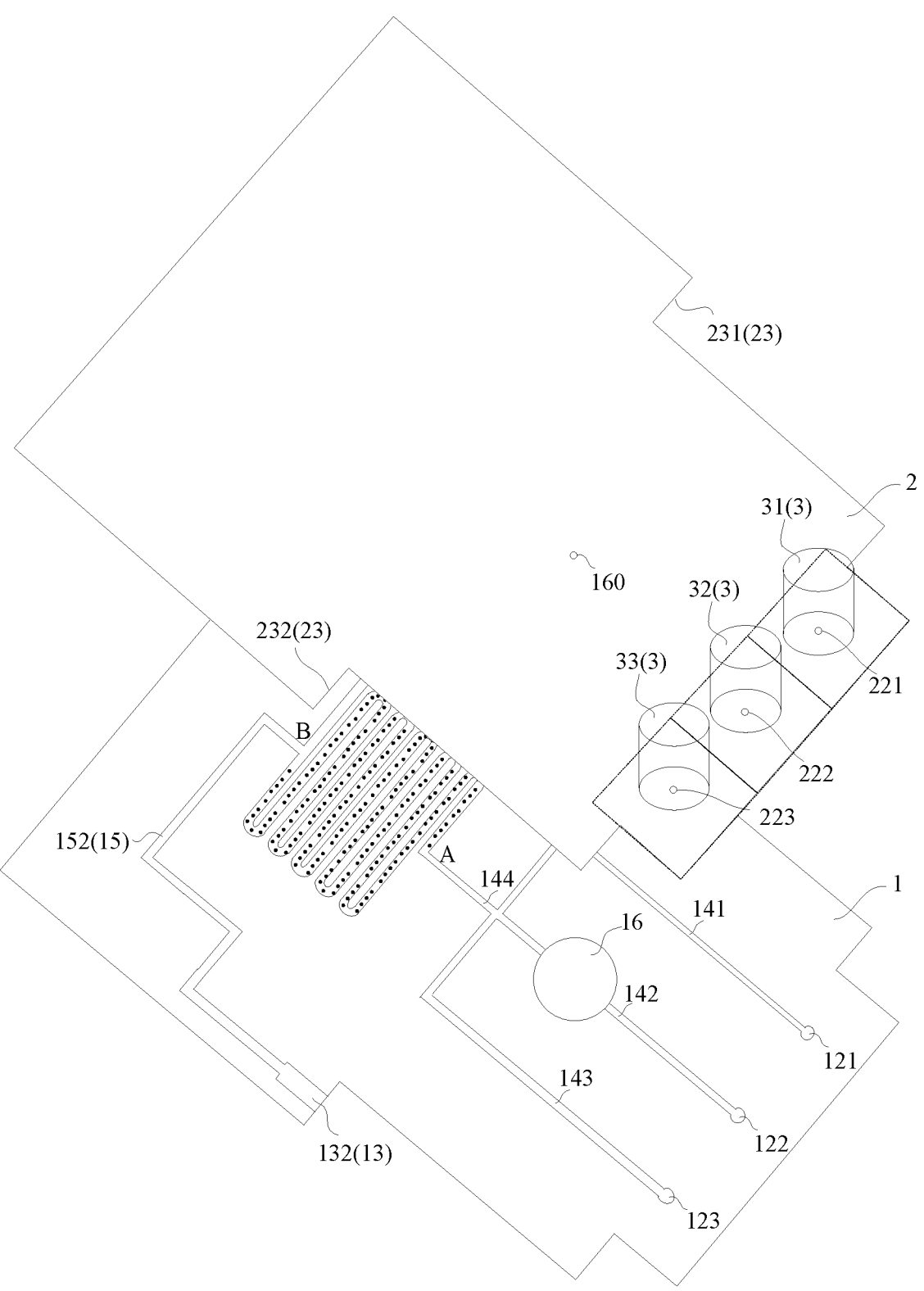
FIG. 3 is a schematic diagram of an overall structure of a nucleic acid extraction microfluidic chip according to embodiments of the present disclosure.

Referring to FIG. 1, a schematic structural diagram of a surface of a channel plate opposite to a cover plate, FIG. 2, a schematic diagram of a surface of the cover plate opposite to the channel plate, and FIG. 3, a schematic diagram of an overall structure of a nucleic acid extraction microfluidic chip. An embodiment of the present disclosure provides the nucleic acid extraction microfluidic chip, including:

a channel plate 1, including: a mixed lysis zone 100, an extraction zone 200 adjacent to the mixed lysis zone 100, a gas-pressure driven port 13 in communication with an exterior, a first type of channel 14 communicating the mixed lysis zone 100 with the extraction zone 200, and a second type of channel 15 communicating the extraction zone 200 with the gas-pressure driven port 13;

a cover plate 2, disposed opposite to the channel plate 1, wherein the cover plate 2 includes a sample inlet 160 and a liquid inlet through hole 22 in a location corresponding to the mixed lysis zone 100; and a solution accommodating cavity 3, located on a side of the cover plate 2 away from the channel plate 1, wherein the solution accommodating cavity 3 communicates with the mixed lysis zone 100 of the channel plate 1 through the liquid inlet through hole 22.

According to the nucleic acid extraction microfluidic chip provided by the embodiments of the disclosure, a sample liquid is injected into the mixed lysis zone 100 through the sample inlet 160 of the cover plate 2, and a lysis solution that can lyse the sample liquid is injected through the solution accommodating cavity 3 into the mixed lysis zone 100. In the mixed lysis zone 100, the sample liquid is lysed by the lysis solution to obtain a nucleic acid, and thereafter, a mixed liquid after lysis in the mixed lysis zone 100 is moved into the extraction zone 200. In the extraction zone 200, the nucleic acid formed after lysis may be adsorbed by a magnetic bead 110 and purified in a flushing mode by injection of a flushing liquid through the solution accommodating cavity 3. When waste liquid that has flushed the magnetic bead is discharged, a magnetic field is applied externally to attract the magnetic bead 110 in the region where the extraction zone 200 is located so as to also attract the nucleic acid and discharge other liquids. An eluent is injected then through the solution accommodating cavity 3, and the eluent may separate the magnetic bead 110 from the nucleic acid, effecting obtaining pure nucleic acid. In contrast to the device for obtaining nucleic acid in prior art, the nucleic acid extraction microfluidic chip provided by the embodiments of the disclosure may lower the risk that may arise from operator contact with exposed samples, the operation flow is simplified, a user does not need to provide an operation container himself, an entire extraction reaction can be completed in the microfluidic chip, errors that may arise from human operation are reduced, and portability is also improved.

During specific implementation, referring to FIG. 1, the extraction zone 200 includes: an extraction trough 11 with a liquid inlet end A and a liquid outlet end B.

The mixed lysis zone 100 includes: a mixed lysis groove 16, as well as a first liquid inlet groove 121, a second liquid inlet groove 122 and a third liquid inlet groove 123 arranged in sequence on one side where the mixed lysis groove 16 is located.

The first type of channel 14 includes: a first channel 141 communicating the first liquid inlet groove 121 with the liquid inlet end A, a second channel 142 communicating the second liquid inlet groove 122 with the liquid inlet end A, and a third channel 143 communicating the third liquid inlet groove 123 with the liquid inlet end A, wherein the mixed lysis groove 16 is located in the second channel 142.

The second type of channel 15 includes: a fourth channel 15 communicating the liquid outlet end B with the gas-pressure driven port 13.

The liquid inlet through hole 22 includes: a first through hole 221 corresponding to the first liquid inlet groove 21, a second through hole 222 corresponding to the second liquid inlet groove 122, and a third through hole 223 corresponding to the third liquid inlet groove 123.

The solution accommodating cavity 3 includes:

a flushing liquid accommodating cavity 31, in communication with the first liquid inlet groove 121 of the channel plate 1 through the first through hole 221;

a lysis solution accommodating cavity 32, in communication with the second liquid inlet groove 122 of the channel plate 1 through the second through hole 222; and an eluent accommodating cavity 33, in communication with the third liquid inlet groove 123 of the channel plate 1 through the third through hole 223.

The magnetic bead 110 is positioned within the extraction trough 11. Specifically, the magnetic bead 110 is a magnetic bead that can adsorb the nucleic acid to be extracted, specifically can be provided with a substance that matches the nucleic acid to allow binding to the nucleic acid.

During specific implementation, the lysis solution accommodating cavity 32, the flushing liquid accommodating cavity 31 and the eluent accommodating cavity 33 in the embodiments of the present disclosure each may be a separate cavity as shown in FIG. 1, and may also have a composite structure including a plurality of sub-cavities. For example, when the lysis solution specifically consists of a plurality of reagents, mixing together the plurality of reagents may affect chemical properties of each agent, in this case, the lysis solution accommodating cavity 32 may include a plurality of discrete lysis solution accommodating sub-cavities, the plurality of lysis solution accommodating sub-cavities may be arranged in a row, and alternatively, may be arranged in a ring, and each lysis solution accommodating sub-cavity may store at least one lysis reagent. For example, the lysis solution accommodating cavity 32 may include a first lysis solution accommodating sub-cavity, a second lysis solution accommodating sub-cavity, and a third lysis solution accommodating sub-cavity. The first lysis solution accommodating sub-cavity may store two lysis reagents with chemical properties not affecting each other (or promoting each other), the second lysis solution accommodating sub-cavity may store three other lysis reagents with chemical properties not affecting each other (or promoting each other), and the third lysis solution accommodating sub-cavity may store two other lysis reagents with chemical properties not affecting each other (or promoting each other).

During specific implementation, the lysis solution accommodating cavity 32, the flushing liquid accommodating cavity 31 and the eluent accommodating cavity 33 may be electrically controlled structures, and bottom portions of these cavities may be provided with electrically heatable Indium tin oxide (ITO) electrodes and bottom wax micro valves that can be electrically heated to melt, so as to release the internal reagents into respective flow channels. The top end faces of the lysis solution accommodating cavity 32, the flushing liquid accommodating cavity 31 and the eluent accommodating cavity 33, e.g., the upper end faces of the cylindrical lysis solution accommodating cavity 32, the flushing liquid accommodating cavity 31 and the eluent accommodating cavity 33 as shown in FIG. 3, may each be provided with an opening (not shown in FIG. 3), and the opening is sealed with waterproof and breathable membranes to allow air to enter when the liquid is driven by the negative pressure so as to allow flow of the liquid within the channels by application of negative pressure. The lysis solution accommodating cavity 32, the flushing liquid accommodating cavity 31 and the eluent accommodating cavity 33 may also be flexible bags to enable release of liquid by squeezing.

During specific implementation, the extraction trough 11 may be of a snake shape, and as such, the volume of the extraction trough 11 may be increased to achieve sufficient mixing of the liquid.

Figure 4A:
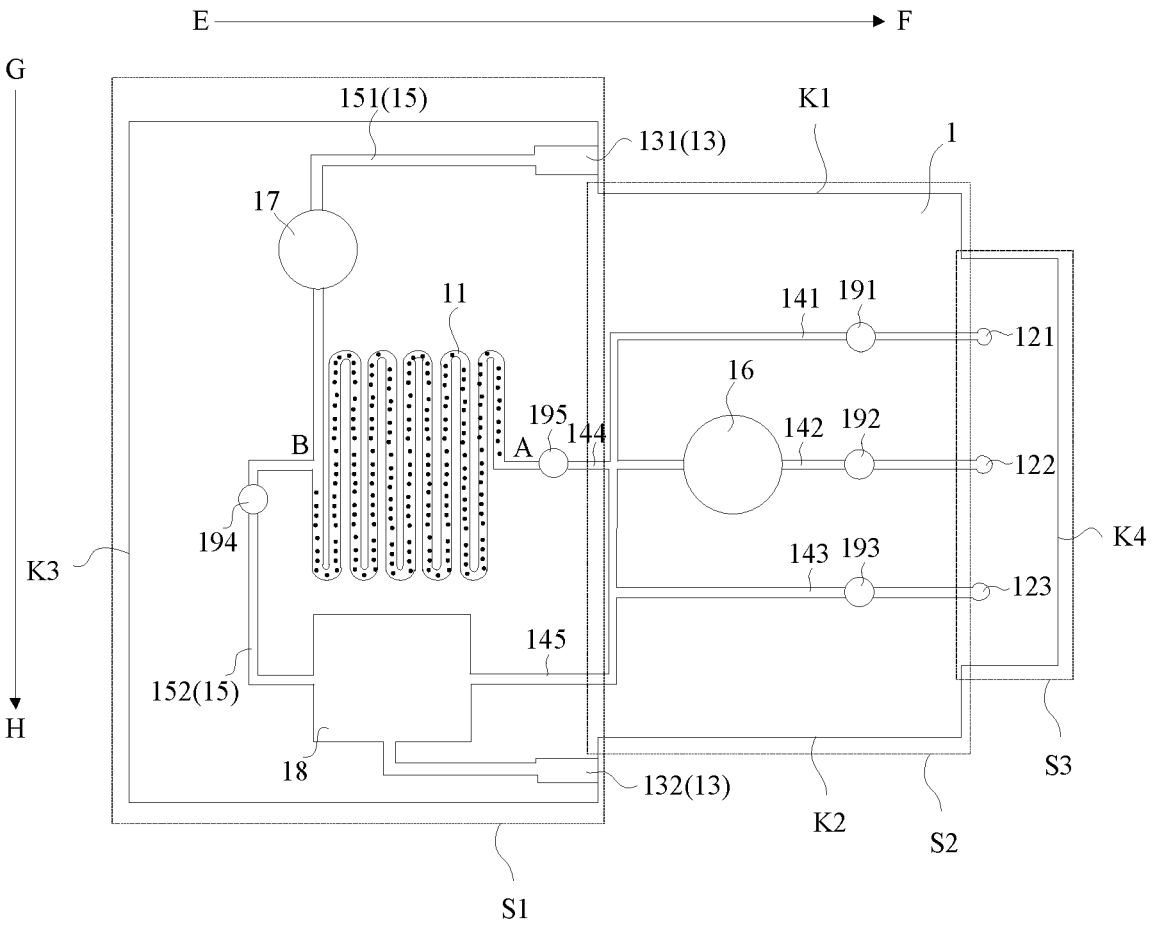
FIG. 4A is a schematic structural diagram of a specific channel plate according to embodiments of the present disclosure.

During specific implementation, as shown in FIG. 1 or FIG. 4A, the gas-pressure driven port 13 includes a first gas-pressure driven port 131 and a second gas-pressure driven port 132. The fourth channel 15 includes: a first sub-channel 151 communicating the first gas-pressure driven port 131 with the liquid outlet end B, and a second sub-channel 152 communicating the second gas-pressure driven port 132 with the liquid outlet end B. During specific implementation, the first gas-pressure driven port 131 may serve as a first negative pressure access port for sucking the lysis solution in the lysis solution accommodating cavity 32 into the mixed lysis groove 16, and for adsorbing liquid in the mixed lysis groove 16 into the extraction trough 11 in subsequent operations, and the second gas-pressure driven port 132 may act as a second negative pressure access port for sucking out liquid that has flushed the magnetic bead into the extraction trough 11. The first gas-pressure driven port 131 and the second gas-pressure driven port 132 of the channel plate 1 may in particular be semi-cylindrical grooves. The cover plate 2 may in particular be provided with semi-cylindrical grooves 23 at positions corresponding to the first gas-pressure driven port 131 and the second gas-pressure driven port 132 of the channel plate 1 (the grooves 23 includes a first corresponding gas-pressure driven port groove 231 corresponding to the first gas-pressure driven port 131 and a second corresponding gas-pressure driven port groove 232 corresponding to the second gas-pressure driven port 132). After the cover plate 2 and the channel plate 1 are oppositely closed with each other, a tubular cavity is formed, and an external piston is used for pulling to form a syringe-like structure, which can achieve the purpose of applying positive or negative pressure to the interior of the nucleic acid extraction microfluidic chip.

Figure 4B:
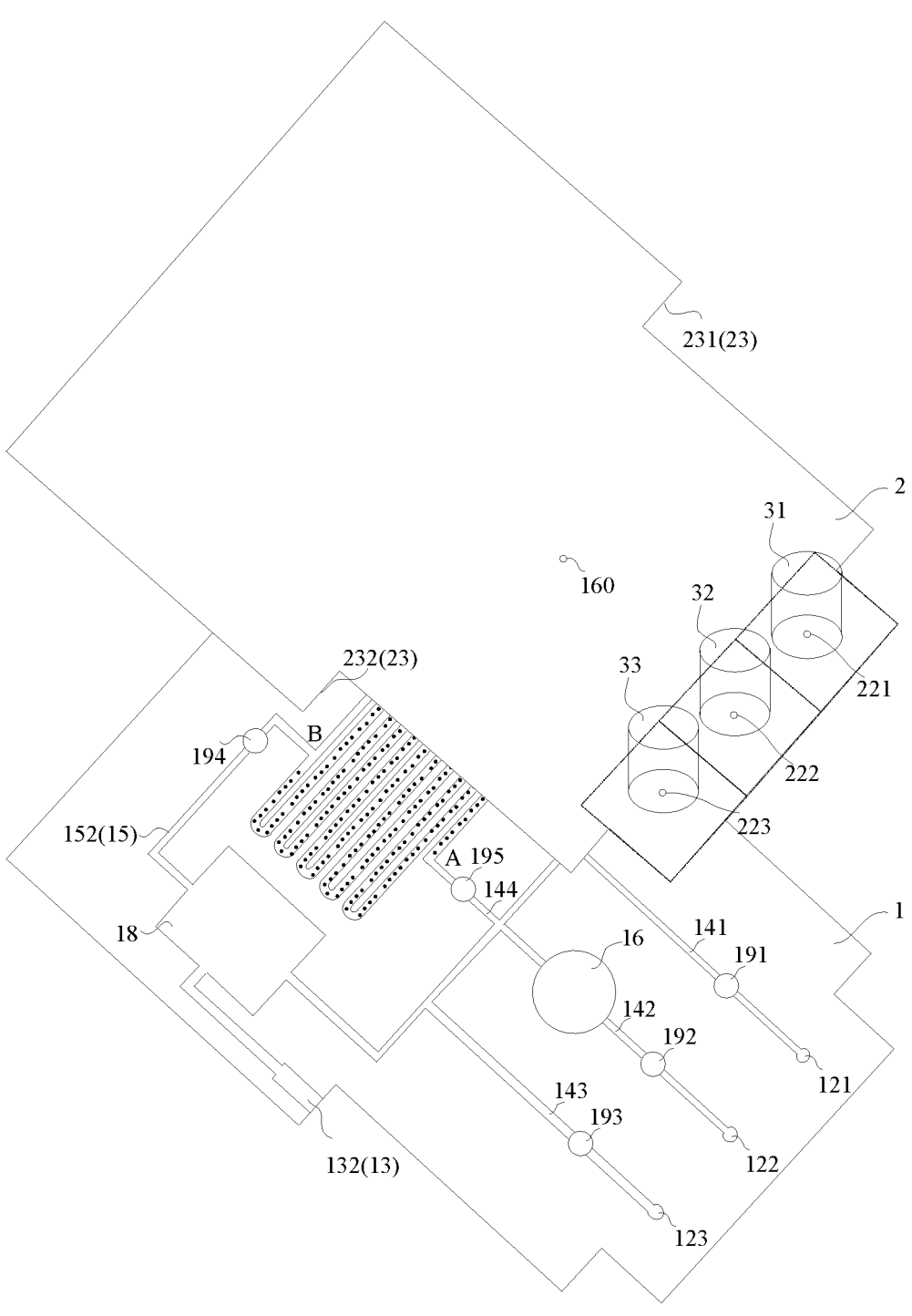
FIG. 4B is a schematic diagram of an overall structure of a specific nucleic acid extraction microfluidic chip according to embodiments of the present disclosure.

During specific implementation, as shown in FIG. 4A and FIG. 4B, the nucleic acid extraction microfluidic chip further includes: a sample storage groove 17 located at the first sub-channel 151, and a waste liquid storage groove 18 located at the second sub-channel 152. In the embodiments of the present disclosure, the nucleic acid extraction microfluidic chip further includes the sample storage groove 17 and the waste liquid storage groove 18, the purified nucleic acid may be sucked into the sample storage groove 17, and waste liquid from the extraction trough 11 during operation may be sucked into the waste liquid storage groove 18.

During specific implementation, as shown in FIG. 4A and FIG. 4B, the first channel 141, the second channel 142 and the third channel 143 converge at a liquid inlet channel 144 to communicate with the liquid inlet end A. The waste liquid storage groove 18 is also in communication with the liquid inlet channel 144 through a fifth channel 145. In the embodiments of the present disclosure, the waste liquid storage groove 18 is also in communication with the liquid inlet channel 144 through the fifth channel 145, in some cases where the magnetic bead 110 are not pre-coated into the extraction trough 11, but rather a magnetic bead solution is stored in a magnetic bead accommodating cavity (which may be configured similarly to the lysis solution accommodating cavity 32 and may be in communication with the mixed lysis groove 16 via a sixth channel, not shown), the magnetic bead may be mixed with the lysis mixed liquid in the mixed lysis groove 16, and for waste liquid obtained after cell lysis, after the magnetic bead is adsorbed by the magnetic supply component, the waste liquid may be drained directly into the waste liquid storage groove 18 without passing through the extraction trough 11 (snake-shaped tube), thereby reducing the possibility of contamination in subsequent operation due to the waste liquid entering the extraction trough 11.

During specific implementation, the magnetic bead 110 may be pre-coated within the extraction trough 11, i.e., the nucleic acid extraction microfluidic chip further includes the magnetic bead 110 positioned within the extraction trough 11. Alternatively, a magnetic bead accommodating cavity for storing the magnetic bead 110 may be provided separately for the magnetic bead, that is, the nucleic acid extraction microfluidic chip further includes: the magnetic bead accommodating cavity (not shown, the arrangement way of the specific structure and the communication way with the extraction trough 11 and the mixed lysis groove 16 may be similar to the lysis solution accommodating cavity 32, the flushing liquid accommodating cavity 31 and the eluent accommodating cavity 33) on one side of the cover plate 2 away from the channel plate 1. Correspondingly, the mixed lysis zone 100 further includes: a fourth liquid inlet groove, and the sixth channel communicating the fourth liquid inlet groove and the liquid inlet end A. The cover plate further includes: a fourth through hole corresponding to the fourth liquid inlet groove. The magnetic bead accommodating cavity is in communication with the fourth liquid inlet groove of the channel plate through the fourth through hole. Alternatively, the magnetic bead 110 may be mixed in the lysis solution accommodating cavity 32 as a lysis solution in the lysis solution accommodating cavity 32.

During specific implementation, as shown in FIG. 4A and FIG. 4B, the first type of channel 14 and the second type of channel 15 are also provided with control valves, and in particular, the control valves include: a first control valve 191 located in the first channel 141; a second control valve 192 located in the second channel 142; a third control valve 193 located in the third channel 143; and a fourth control valve 194 located in the second sub-channel 152 and located between the waste liquid storage groove 18 and the liquid outlet end B. In the embodiments of the present disclosure, the first control valve 191, the second control valve 192, the third control valve 193 and the fourth control valve 194 are initially in an open state. The second control valve 192 may be controlled to close before the flushing liquid in the flushing liquid accommodating cavity 31 is sucked into the extraction trough 11 through the first gas-pressure driven port 131 to avoid insufficient negative pressure due to air leakage in the second channel 142 (i.e. the channel in which the second control valve 192 is located) when the first channel 141 needs to be introduced negative pressure to drive the liquid. The first control valve 191 may be controlled to close before the flushing liquid in the eluent accommodating cavity 33 is sucked into the extraction trough 11 through the first gas-pressure driven port 131 to avoid insufficient negative pressure due to air leakage in the first channel 141 (i.e. the channel in which the first control valve 191 is located) when the third channel 143 needs to be introduced negative pressure to drive the liquid. After the flushing liquid is released from the eluent accommodating cavity 33, the third control valve 193 can remain open so that positive or negative pressure can subsequently be applied to the channel. Prior to sucking the purified nucleic acid into the sample storage cavity 17, the fourth control valve 194 may be controlled to close to avoid sucking waste liquid in the waste liquid storage cavity 18 into the sample storage cavity 17.

During specific implementation, the nucleic acid extraction microfluidic chip further includes: a fifth control valve 195 located at the liquid inlet channel 144.

Figure 5A:
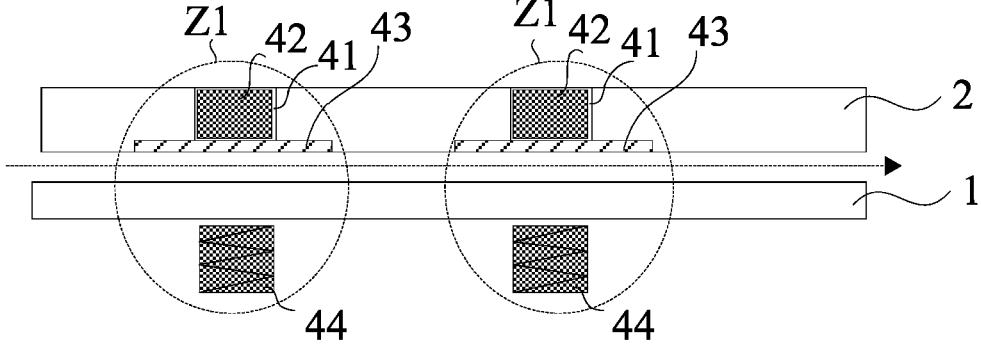
FIG. 5A is a schematic diagram of an opened solenoid control valve structure according to embodiments of the present disclosure.
Figure 5B:
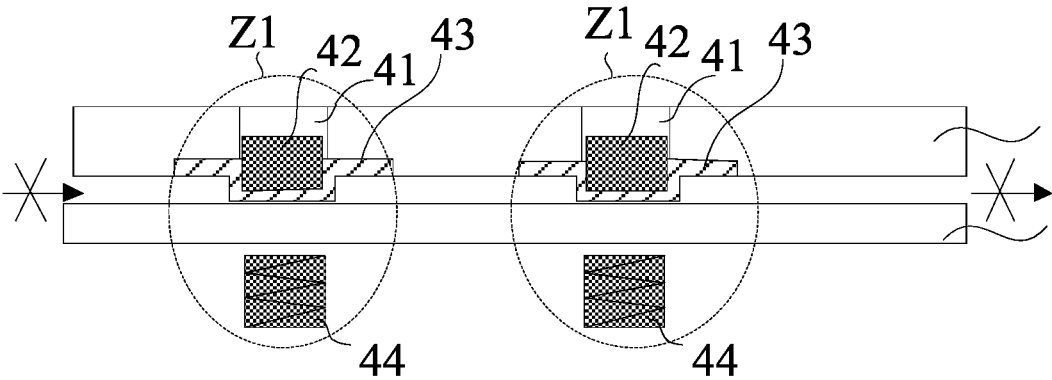
FIG. 5B is a schematic diagram of a closed solenoid control valve structure according to embodiments of the present disclosure.
Figure 5C:
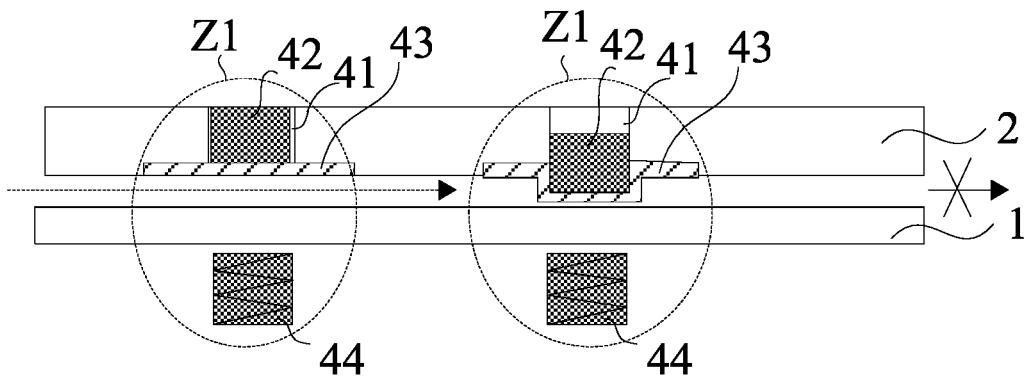
FIG. 5C is a schematic diagram of a solenoid control valve structure which is partially opened and partially closed according to embodiments of the present disclosure.

During specific implementation, referring to FIG. 5A, FIG. 5B, FIG. 5C and FIG. 6, the control valve is a solenoid control valve structure Z1, that is, at least one of the first control valve 191, the second control valve 192, the third control valve 193 and the fourth control valve 194 is the solenoid control valve structure Z1. The solenoid control valve structure Z1 includes: an iron block accommodating groove 41 in a surface of the cover plate 2 facing the channel plate 1, an iron block 42 located in the iron block accommodating groove 41, and an elastic protective membrane 43 sealing the iron block accommodating groove 41 on a side of the iron block 42 facing the channel plate 1. During specific implementation, an electromagnet 44 may be further arranged on a side of the channel plate 1 away from the cover plate 2, and the electromagnet 44 specifically may be a structure independent from the nucleic acid extraction microfluidic chip. When liquid is required to flow through the position where the solenoid control valve structure Z is located, the electromagnet 44 may be controlled to be powered off and the iron block 42 is located entirely within the iron block accommodating groove 41, so that the liquid can pass in an unobstructed mode, as shown in FIG. 5A. When it is required that the liquid cannot flow through the position where the solenoid control valve structure Z1 is located, the electromagnet 44 may be controlled to be powered on in a forward direction and the iron block 42 in the iron block accommodating groove 41 is adsorbed by the electromagnet 44 to block the flow of the liquid, as shown in FIG. 5B. When it is required that the liquid can flow through a position where a part of the solenoid control valve structures Z1 are located (e.g., liquid flow is required at the left position in FIG. 5C), while the liquid is blocked at a position where other solenoid control valve structures Z1 are located (e.g., the liquid needs to be blocked at the right position in FIG. 5C), the electromagnet 44 at the position where the liquid needs to flow may be controlled to be powered off or powered on in a reverse direction to cause the liquid to flow through, while the electromagnet 44 is controlled to be powered on in the forward direction for the solenoid control valve structure Z1 at the position where liquid flow is required to be blocked, so that the iron block 42 within the iron block accommodating groove 41 is adsorbed by the electromagnet 44 to block liquid flow, as shown in FIG. 5C. At least one of the first control valve 191, the second control valve 192, the third control valve 193 and the fourth control valve 194 is the solenoid control valve structure Z1, so that the nucleic acid extraction microfluidic chip may have a small device size and a better portability.

Figure 7A:
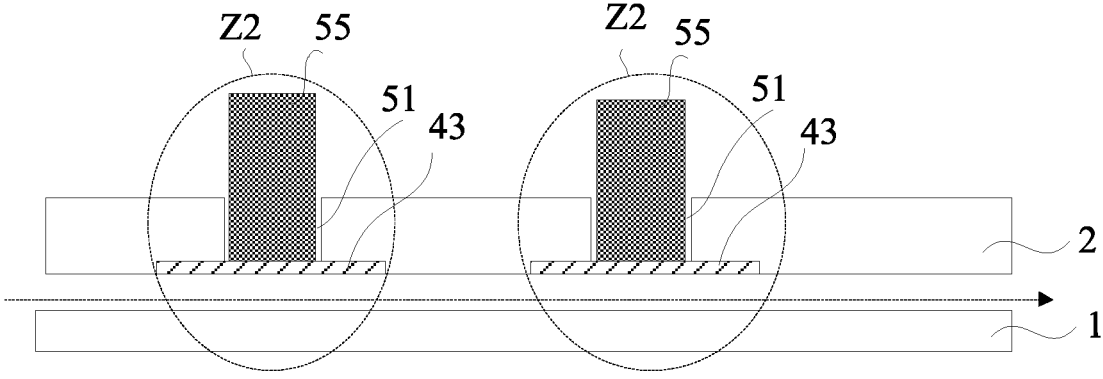
FIG. 7A is a schematic diagram of an opened camshaft pressing rod valve according to embodiments of the present disclosure.
Figure 7B:
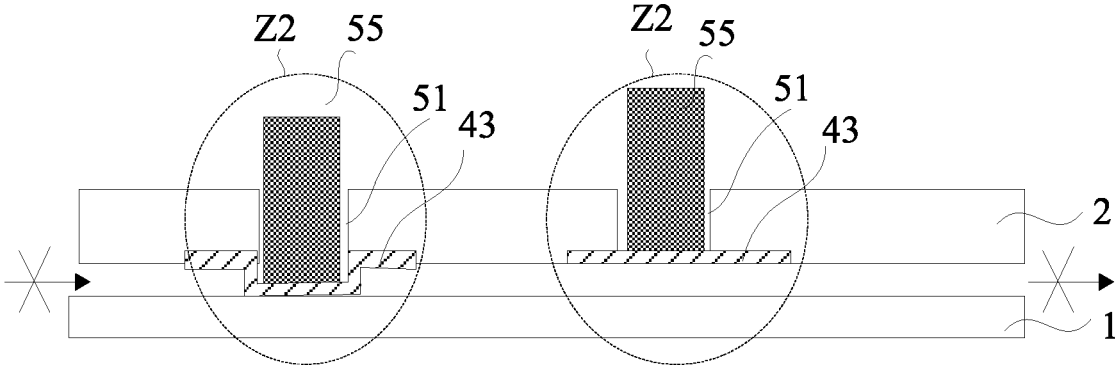
FIG. 7B is a schematic diagram of a camshaft pressing rod valve which is partially opened and partially closed according to embodiments of the present disclosure.

During specific implementation, as shown in FIG. 7A, FIG. 7B, FIG. 7C and FIG. 8, the control valve is a solenoid control valve structure Z2, that is, at least one of the first control valve 191, the second control valve 192, the third control valve 193 and the fourth control valve 194 is a camshaft pressing rod valve structure Z2. The camshaft pressing rod valve structure Z2 includes an accommodating rod through groove 51 in a surface of the cover plate 2 away from the channel plate 1 and an elastic protective membrane 43 on a side of the accommodating rod through channel 51 facing the channel plate 1. During specific implementation, the camshaft pressing rod valve structure Z2 may cooperate with an external camshaft 56, a pressing rod 55 and a connecting rod 57 connecting the pressing rod 55 and the camshaft 56 to pull up or down to block the liquid or enable the liquid to circulate at the position where the camshaft pressing rod valve structure Z2 is located. As shown in FIG. 7A, during upward pulling, liquid circulation may be achieved. As shown in the camshaft pressing rod valve structure Z2 on the left side of FIG. 7B, during down pulling, the liquid may be blocked. The camshaft 56 can specifically rotate, and different pressing rods 55 may specifically be at different fixed angles from the camshaft to achieve pull-up or pull-down of the pressing rods 55 at different positions. The end of the connecting rod 57 connected to the pressing rod 55 may be provided with a suction cup to absorb the pressing rod 55. At least one of the first control valve 191, the second control valve 192, the third control valve 193 and the fourth control valve 194 is the electric camshaft pressing rod valve structure Z2, so that the nucleic acid extraction microfluidic chip may have higher reliability.

Figure 9A:
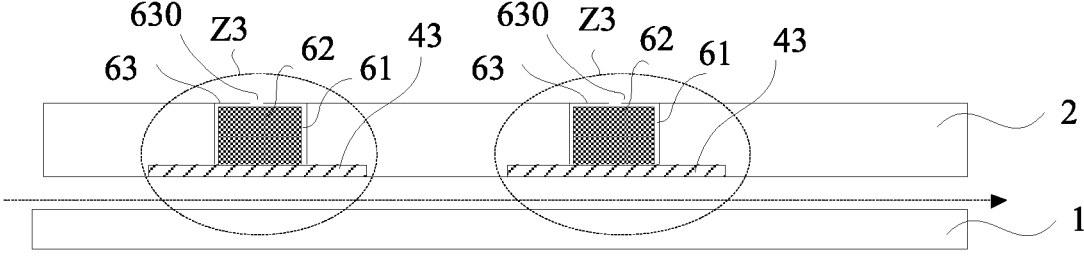
FIG. 9A is a schematic diagram of an opened gas-pressure driven squeezing valve structure according to embodiments of the present disclosure.
Figure 9B:
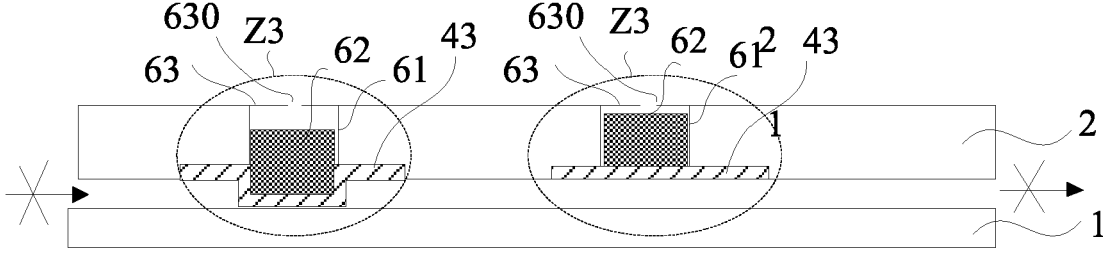
FIG. 9B is a schematic diagram of a gas-pressure driven squeezing valve structure which is partially opened and partially closed according to embodiments of the present disclosure.
Figure 10:
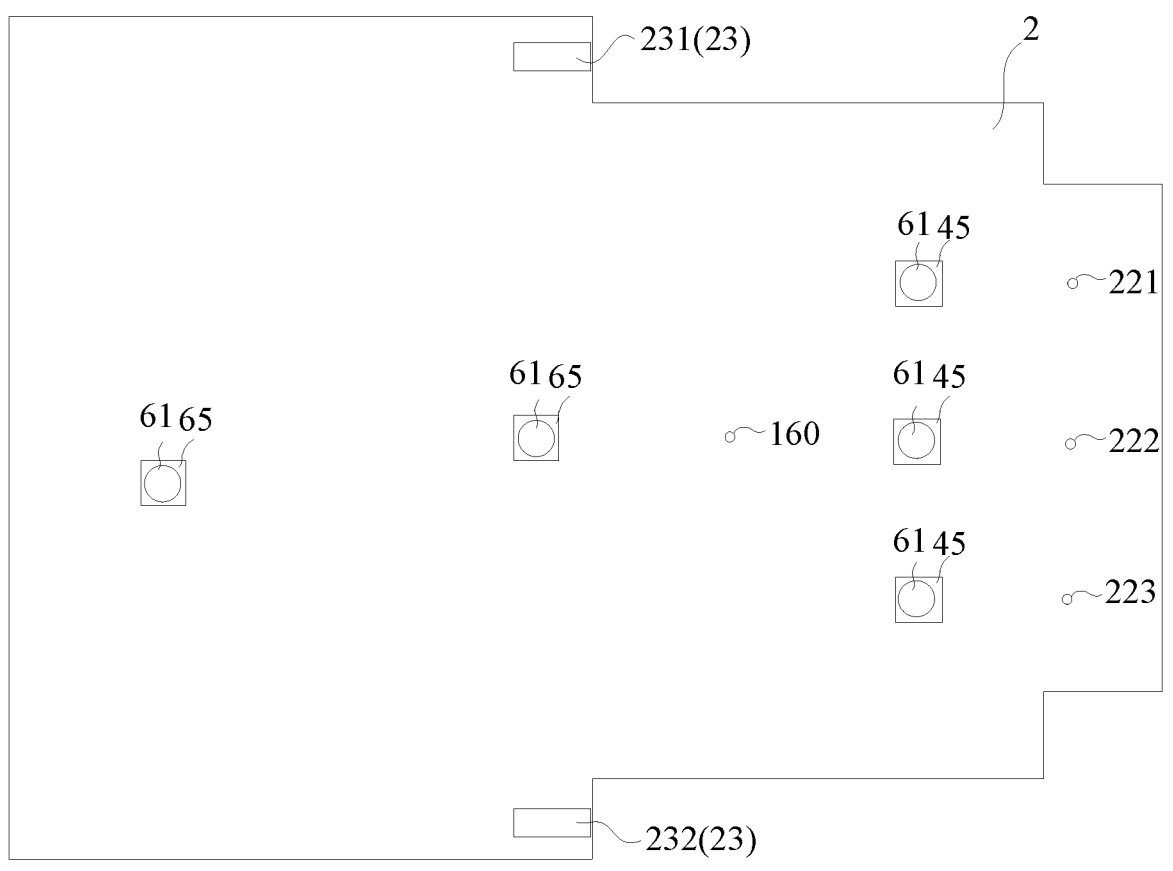
FIG. 10 is a schematic structural diagram that a cover plate with a gas-pressure driven squeezing valve structure, according to embodiments of the present disclosure.

During specific implementation, as shown in FIG. 9A, FIG. 9B and FIG. 10, the control valve is a solenoid control valve structure Z3, that is, at least one of the first control valve 191, the second control valve 192, the third control valve 193 and the fourth control valve 194 is a gas-pressure driven squeezing valve structure Z3. The gas-pressure driven squeezing valve structure Z3 includes: a squeezing block accommodating groove 61 in a surface of the cover plate 2 away from the channel plate 1, a squeezing block 62 located in the squeezing block accommodating groove 61, a bottom membrane 63 located on a side of the squeezing block 62 away from the channel plate 1, and an elastic protective membrane 43 located on a side of the squeezing block 62 facing the channel plate 1. The bottom membrane 63 includes a gas circuit access port 630 communicating with the squeezing block accommodating groove 61. During specific implementation, gas can be introduced through the gas circuit access port 630, so that the squeezing block 62 squeezes the elastic protective membrane 43, and then liquid at the positions where different gas-pressure driven squeezing valve structures Z3 are located circulates or is blocked. For example, positive pressure is applied to the gas-pressure driven squeezing valve structure Z3 on the left in FIG. 9B to cause the squeezing block 62 to squeeze the elastic protective membrane 43 to block liquid, and negative or zero pressure is applied to the gas-pressure driven squeezing valve structure Z3 on the right in FIG. 9B to enable the liquid to circulate.

Figure 6:
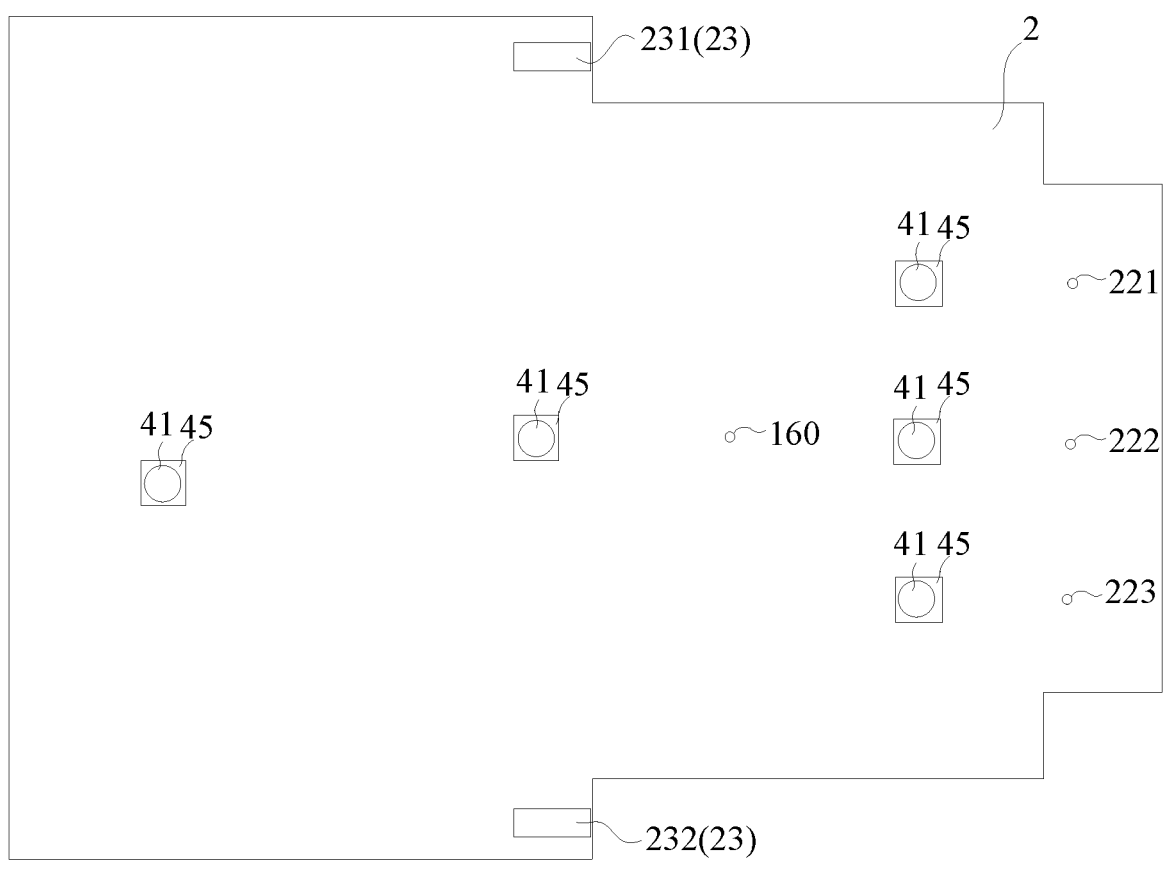
FIG. 6 is a schematic structural diagram that a cover plate with a solenoid control valve structure according to embodiments of the present disclosure.
Figure 8:
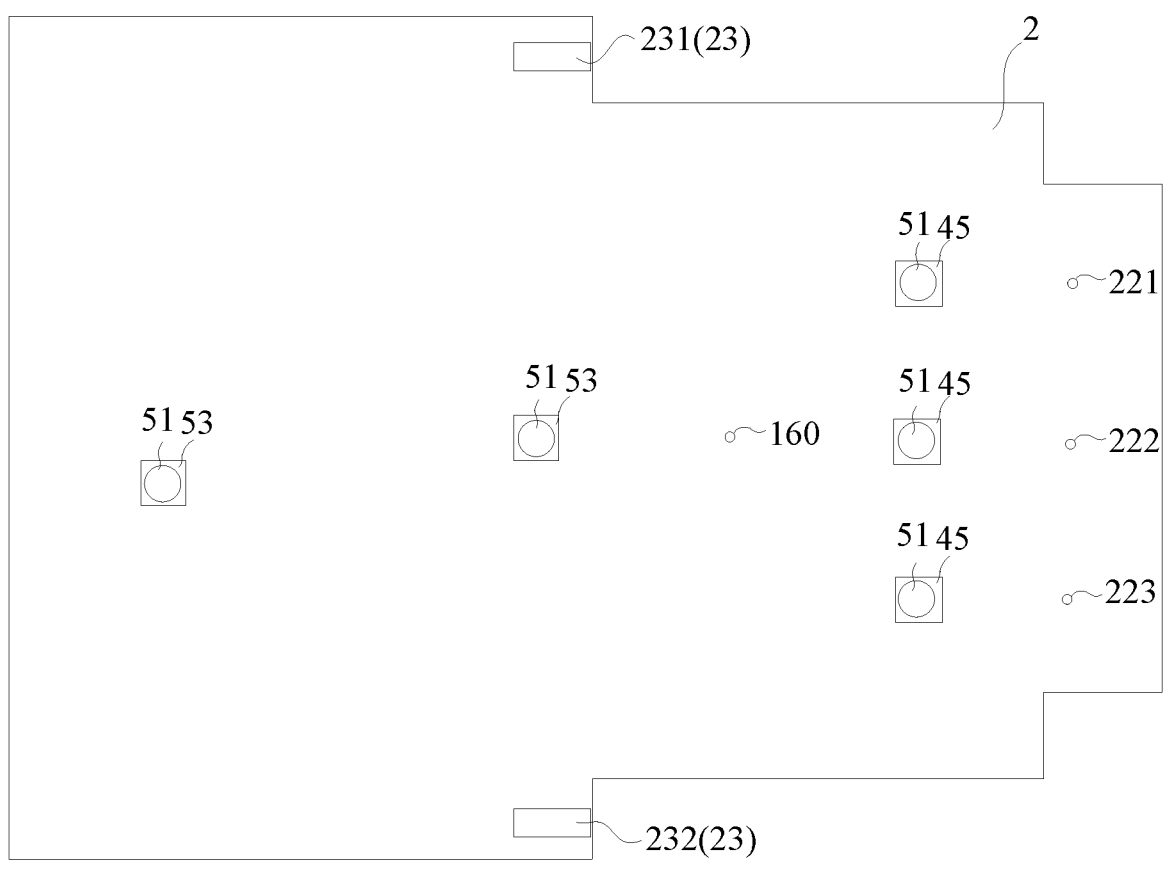
FIG. 8 is a schematic structural diagram that a cover plate with a camshaft pressing rod valve, according to embodiments of the present disclosure.

During specific implementation, as shown in FIG. 6, FIG. 8 and FIG. 10, a surface of the cover plate 2 facing the channel plate 1 is also provided, with a protective membrane accommodating groove 45 for accommodating the elastic protective membrane 43, and an orthographic projection of the protective membrane accommodating groove 45 on the cover plate 2 covers an orthographic projection of the elastic protective membrane 43 on the cover plate 2. Specifically, the orthographic projection of the protective membrane accommodating groove 45 on the cover plate 2 is rectangular, and the orthographic projection of the protective membrane accommodating groove 45 on the cover plate 2 coincides with the orthographic projection of the elastic protective membrane 43 on the cover plate 2.

During specific implementation, a material of the elastic protective membrane 43 is polydimethylsiloxane (PDMS). Specifically, the thickness of the elastic protective membrane 43 is between 90 μm and 110 μm to give the elastic protective membrane 43 better resilience, longer use duration and higher response speed.

During specific implementation, as shown in FIG. 4A, a main body shape of the channel plate 1 is a rectangle, and the channel plate includes a first side edge K1 and a second side edge K2 extending in a first direction EF, and a third side edge K3 and a fourth side edge K4 extending in a second direction GH. The shape of the cover plate 2 is the same as the shape of the channel plate 1. The channel plate 1 includes a first segment S1, a second segment S2 and a third segment S3 arranged in sequence in the first direction EF, and lengths of the first segment S1, the second segment S2 and the third segment S3 in the second direction GH decrease in sequence. The first gas-pressure driven port 131 is located at a position, where the first segment S1 protrudes more than the second segment S2, of the first side edge K1, and the second gas-pressure driven port 132 is located at a position, where the first segment S1 protrudes more than the second segment S2, of the second side edge K2, so that the gas-pressure driven port 13 is substantially at the same level as each of the channels for rapid venting or pumping of air into each of the channels via the gas-pressure driven port 13.

During specific implementation, the sample storage groove 17, the extraction trough 11 and the waste liquid storage groove 18 are located at the first segment S1. The mixed lysis groove 16 is located at the second segment S2. The lysis solution accommodating cavity 32, the flushing liquid accommodating cavity 31, and the eluent accommodating cavity 33 are located in the region where the third segment S3 is located.

During specific implementation, the width of the internal channels (including the first channel 141, the second channel 142, the third channel 143, the first sub-channel 151, the second sub-channel 152, and the liquid inlet channel 144) of the nucleic acid extraction microfluidic chip in the direction perpendicular to their extension directions may be 0.4 mm to 0.6 mm, specifically 0.5 mm; the depth in the direction perpendicular to the channel plate 1 is 0.4 mm to 0.6 mm, specifically 0.5 mm; and the depth of the protective membrane accommodating groove 45 on the cover plate 2 in the direction perpendicular to the cover plate 2 is a recess of the order of hundreds microns for placing an equal-thickness PDMS elastic protective membrane 43. The PDMS elastic membrane adopted in the embodiments of the present disclosure has the thickness of approximately 100 μm, and correspondingly, the protective membrane accommodating groove also has the depth of 100 μm.

During specific implementation, bonding of the cover plate 2 to the channel plate 1 may be achieved by ultrasonic welding or double-sided gluing.

Since the first control valve 191, the second control valve 192, the third control valve 193 and the fourth control valve 194 are consumable devices, there are certain requirements on the thickness and elasticity of the PDMS membrane layers in the first control valve 191, the second control valve 192, the third control valve 193 and the fourth control valve 194, and the embodiments of the present disclosure has an exploration scheme and a solution as follows.

A. A curing agent for making the PDMS membrane layer and a stock solution for making the PDMS membrane layer are mixed in 1:10, glue dripping is performed in a spin coater at 1000 rpm after uniform mixing, thermoforming in a 100° C. drying oven is performed, and after a membrane layer is stabilized, a test membrane layer is taken out, wherein the thickness of the test membrane layer is approximately 150 μm.

B. A curing agent and a stock solution are mixed in 1:5, glue dripping is performed in a spin coater at 1000 rpm after uniform mixing, thermoforming in a 100° C. drying oven is performed, and after a membrane layer is stabilized, a test membrane layer is taken out, wherein the thickness of the test membrane layer is approximately 200 μm.

C. A curing agent and a stock solution are mixed in 1:10, glue dripping is performed in a spin coater at 1500 rpm after uniform mixing, thermoforming in a 100° C. drying oven is performed, and after a membrane layer is stabilized, a test membrane layer is taken out, wherein the thickness of the test membrane layer is approximately 100 μm.

D. A curing agent and a stock solution are mixed in 1:5, glue dripping is performed in a spin coater at 1500 rpm after uniform mixing, thermoforming in a 100° C. drying oven is performed, and after a membrane layer is stabilized, a test membrane layer is taken out, wherein the thickness of the test membrane layer is approximately 170 μm.

E. A curing agent and a stock solution are mixed in 1:10, glue dripping is performed in a spin coater at 1800 rpm after uniform mixing, thermoforming in a 100° C. drying oven is performed, and after a membrane layer is stabilized, a test membrane layer is taken out, wherein the thickness of the test membrane layer is approximately 60 μm.

F. A curing agent and a stock solution are mixed in 1:5, glue dripping is performed in a spin coater at 1800 rpm after uniform mixing, thermoforming in a 100° C. drying oven is performed, and after a membrane layer is stabilized, a test membrane layer is taken out, wherein the thickness of the test membrane layer is approximately 90 μm.

The PDMS membrane layers under four different conditions of A, B, C and D above are used respectively to make the elastic protective membranes in the first control valve 191, the second control valve 192, the third control valve 193 and the fourth control valve 194, the pull-down properties of the first control valve 191, the second control valve 192, the third control valve 193 and the fourth control valve

194 during closing and the resilient properties and the service lives of the control valves during opening are observed, and results are as follows.

A. When the electromagnet is powered on, the time for the membrane layer to be pulled down to close is approximately 2.7 s; when the electromagnet is powered off, the time for the membrane layer to recover from deformation is approximately 0.8 s; and after 50 cycles of power on and off, the membrane layer is not broken and the property of which is not changed.

B. When the electromagnet is powered on, the time for the membrane layer to be pulled down to close is 3.2 s; when the electromagnet is powered off, the time for the membrane layer to recover from deformation is 0.4 s; and after 50 cycles of power on and off, the membrane layer is not broken and the property of which is not changed.

C. When the electromagnet is powered on, the time for the membrane layer to be pulled down to close is 1 s; when the electromagnet is powered off, the time for the membrane layer to recover from deformation is 1 s; and after 50 cycles of power on and off, the membrane layer is not broken and the property of which is not changed.

D. When the electromagnet is powered on, the time for the membrane layer to be pulled down to close is 1.6 s; when the electromagnet is powered off, the time for the membrane layer to recover from deformation is 0.7 s; and after 50 cycles of power on and off, the membrane layer is not broken and the property of which is changed (permanent deformation).

E. When the electromagnet is powered on, the time for the membrane layer to be pulled down to close is 0.4 s; when the electromagnet is powered off, the time for the membrane layer to recover from deformation is 1.2 s; and after 50 cycles of power on and off, the membrane layer is broken due to the small thickness and the property is not changed.

F. When the electromagnet is powered on, the time for the membrane layer to be pulled down to close is 1.1 s; when the electromagnet is powered off, the time for the membrane layer to recover from deformation is 0.9 s; and after 50 cycles of power on and off, and due to excessive hardness/rigidity and small thickness of the membrane layer, the membrane layer is not broken but are difficult to recover from deformation, and the property is changed.

According to the PDMS membrane layers obtained through different compositions and spin coating conditions, it is basically known that C is the best implementation solution, the needs for the elasticity, rigidity and service life can be all considered, the response speed is fast, and thus C is the solution for making elastic layer materials of the first control valve 191, the second control valve 192, the third control valve 193 and the fourth control valve 194 employed by the embodiments of the present disclosure.

Based on the same disclosure concept, an embodiment of the present disclosure further provides a nucleic acid extraction device including the nucleic acid extraction microfluidic chip as provided by the embodiments of the present disclosure. The nucleic acid extraction device further includes a magnetic supply component providing a magnetic field to absorb the magnetic bead 110 to or separate the magnetic bead 110 from the tube wall of the extraction trough 11, as desired.

During specific implementation, as shown in FIG. 5A, FIG. 5B and FIG. 6, when a control valve is a solenoid control valve structure Z1, the nucleic acid extraction device further includes an electromagnet 44.

Figure 7C:
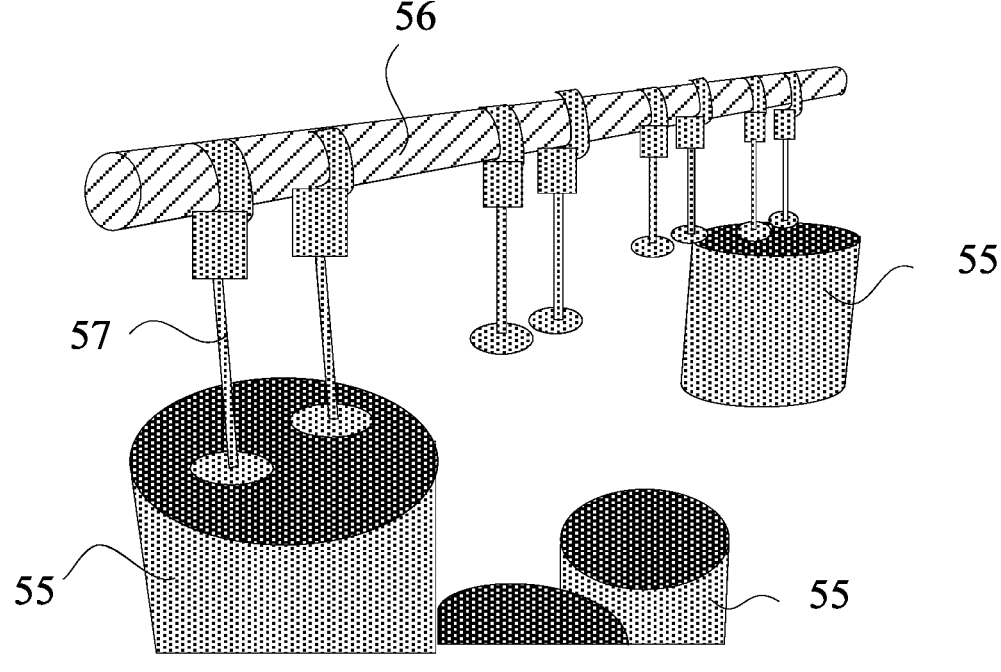
FIG. 7C is a schematic structural diagram of a camshaft corresponding to a camshaft pressing rod valve structure according to embodiments of the present disclosure.

During specific implementation, as shown in FIG. 7C, when the control valve is a camshaft pressing rod valve structure Z2, the nucleic acid extraction device further includes a camshaft 56, and a plurality of pressing rods 55 connected to the camshaft 56.

Figures 11A, 11B:
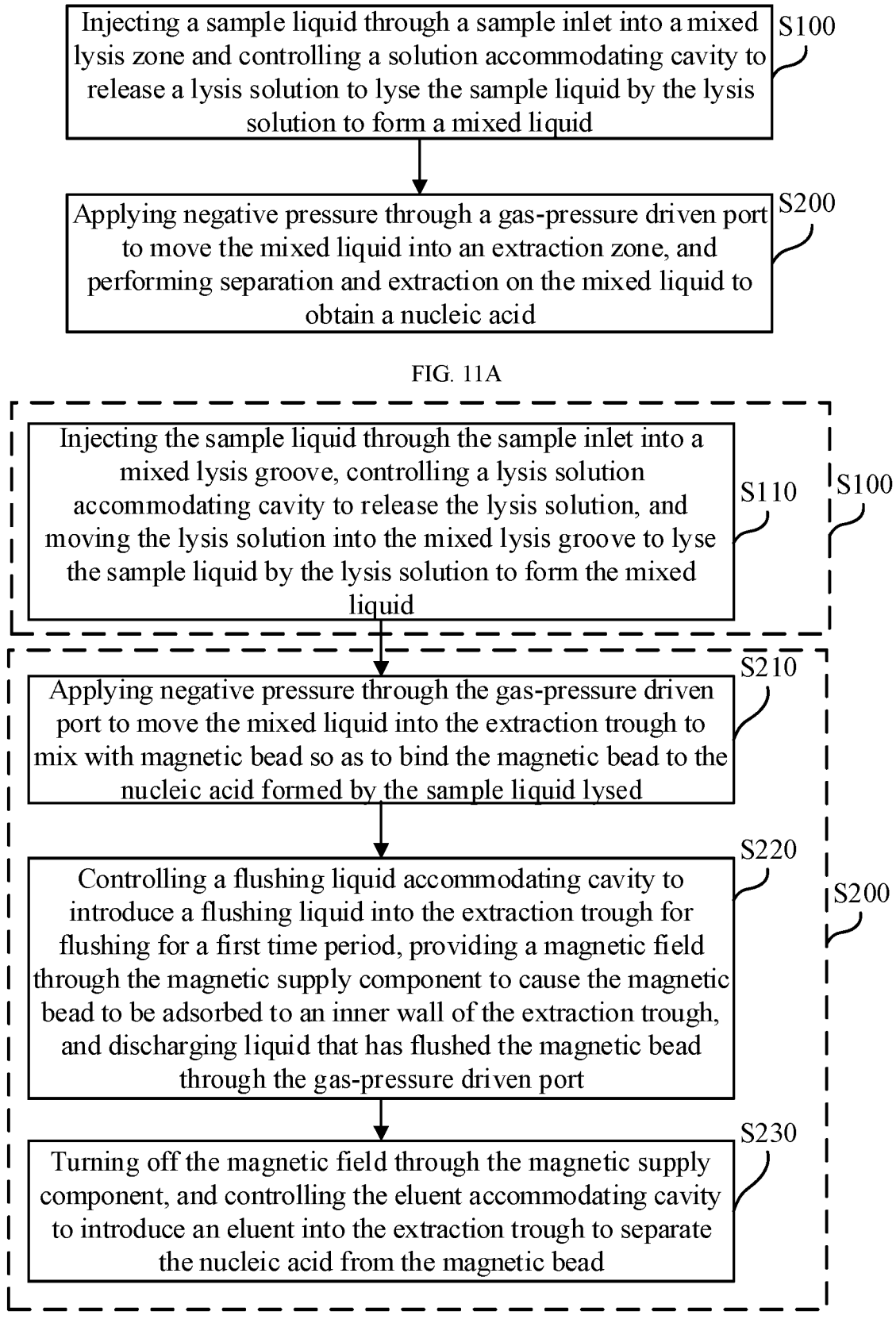
FIG. 11A is a schematic flow diagram of a nucleic acid extraction method according to embodiments of the present disclosure.
FIG. 11B is a schematic flow diagram of a specific nucleic acid extraction method according to embodiments of the present disclosure.

Referring to FIG. 11A, an embodiment of the present disclosure further provides a nucleic acid extraction method of the nucleic acid extraction device provided by the embodiment of the present disclosure, including the following steps.

Step S100, a sample liquid is injected through a sample inlet into a mixed lysis zone and a solution accommodating cavity is controlled to release a lysis solution to lyse the sample liquid by the lysis solution to form a mixed liquid.

Step S200, negative pressure is applied through a gas-pressure driven port to move the mixed liquid into an extraction zone, and separation and extraction are performed on the mixed liquid to obtain a nucleic acid.

During specific implementation, referring to FIG. 11B, step S100 that the sample liquid is injected through the sample inlet into the mixed lysis zone and the solution accommodating cavity is controlled to release the lysis solution may include, step S110, the sample liquid is injected through the sample inlet into the mixed lysis groove, the lysis solution accommodating cavity is controlled to release the lysis solution, and the lysis solution is moved into the mixed lysis groove to lyse the sample liquid by the lysis solution to form the mixed liquid.

Step S200 that negative pressure is applied through the gas-pressure driven port to move the mixed liquid into the extraction zone, and separation and extraction are performed on the mixed liquid to obtain the nucleic acid, may specifically include the following steps.

Step S210, the negative pressure is applied through the gas-pressure driven port to move the mixed liquid into the extraction trough to mix with the magnetic bead so as to bind the magnetic bead to the nucleic acid formed by the sample liquid lysed.

Step S220, the flushing liquid accommodating cavity is controlled to introduce a flushing liquid into the extraction trough for flushing for a first time period, the magnetic field is provided through the magnetic supply component to cause the magnetic bead to be adsorbed to an inner wall of the extraction trough, and liquid that has flushed the magnetic bead is discharged through the gas-pressure driven port. In particular, the nucleic acid extraction microfluidic chip further includes the waste liquid storage groove; and the step that the liquid that has flushed the magnetic bead is discharged through the gas-pressure driven port in step 220 includes: the liquid that has flushed the magnetic bead is discharged into the waste liquid storage groove through the gas-pressure driven port.

Step S230, the magnetic field is turned off through the magnetic supply component, and the eluent accommodating cavity is controlled to introduce an eluent into the extraction trough to separate the nucleic acid from the magnetic bead.

Figure 12:
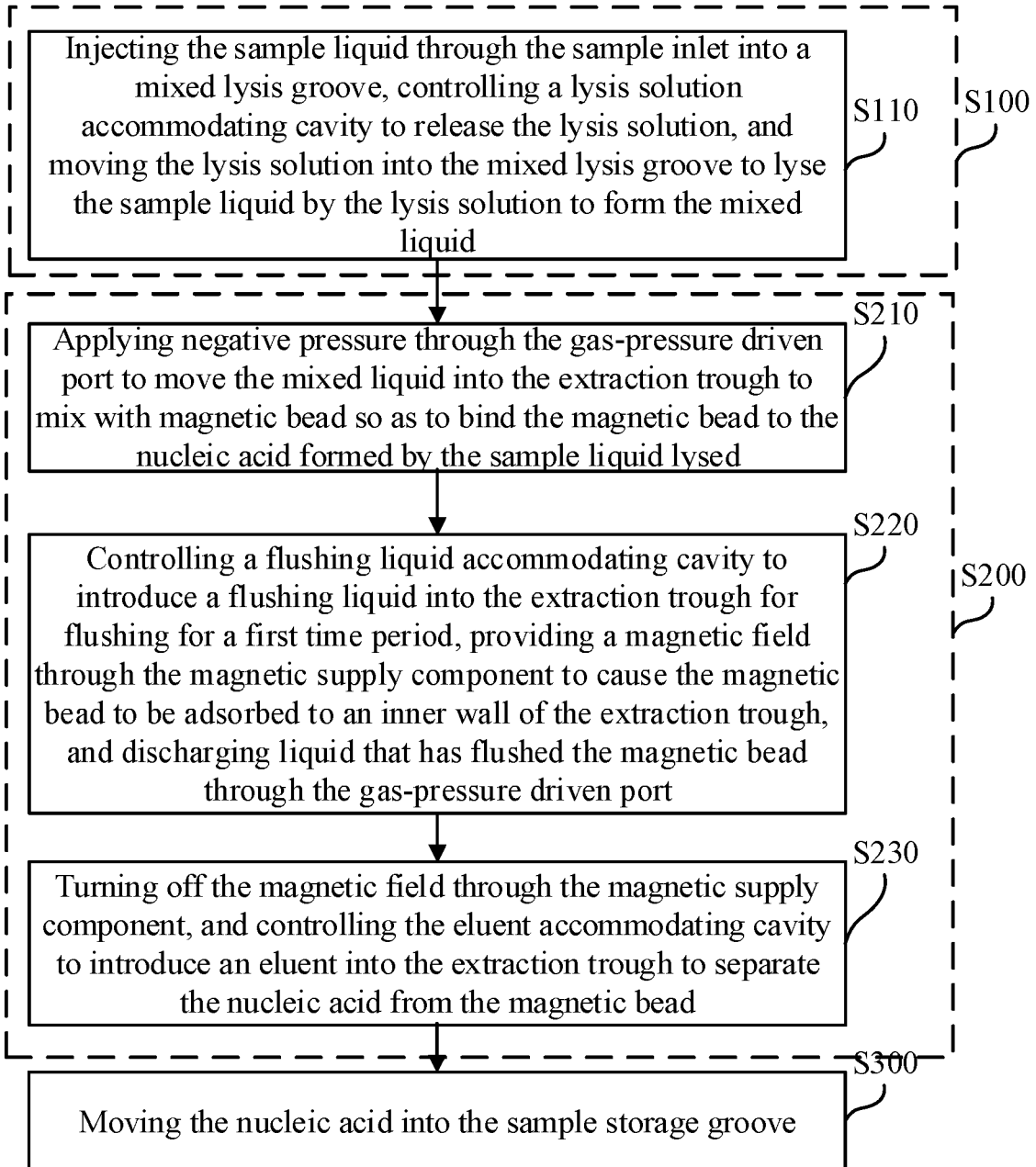
FIG. 12 is a schematic flow diagram of a specific nucleic acid extraction method according to embodiments of the present disclosure.

During specific implementation, referring to FIG. 12, the channel plate further includes the sample storage groove. After step S230 that the eluent accommodating cavity is controlled to introduce the eluent into the extraction trough to separate the nucleic acid from the magnetic bead, as shown in FIG. 12, the nucleic acid extraction method further includes: step S300, the nucleic acid is moved into the sample storage groove.

During specific implementations, the gas-pressure driven port includes a first gas-pressure driven port and a second gas-pressure driven port.

Moving the lysis solution into the mixed lysis groove in step S110 includes: the lysis solution is sucked into the mixed lysis groove by applying negative pressure to the first gas-pressure driven port.

Applying the negative pressure through the gas-pressure driven port to move the mixed liquid into the extraction trough to mix with the magnetic bead in step S210 includes: negative pressure is applied to the first gas-pressure driven port to move the mixed liquid into the extraction trough to mix with the magnetic bead.

Discharging the liquid that has flushed the magnetic bead through the gas-pressure driven port in step S220 includes: the liquid that has flushed the magnetic bead is sucked into the waste liquid storage groove by applying negative pressure to the second gas-pressure driven port.

Introducing the nucleic acid into the sample storage cavity in step S300 includes: the nucleic acid is sucked into the sample storage groove by applying negative pressure to the first gas-pressure driven port.

During specific implementation, the nucleic acid extraction microfluidic chip further includes: a first control valve, a second control valve, a third control valve and a fourth control valve.

Prior to step S100 that the sample liquid is injected through the sample inlet into the mixed lysis groove, the nucleic acid extraction method further includes: the first control valve, the second control valve, the third control valve and the fourth control valve are opened.

Prior to controlling the flushing liquid accommodating cavity to introduce the flushing liquid into the extraction trough, the nucleic acid extraction method further includes: the second control valve is closed.

Prior to controlling the eluent accommodating cavity to introduce the eluent into the mixed lysis groove, the nucleic acid extraction method further includes: the first control valve is closed.

Prior to moving the nucleic acid into the sample storage groove, the nucleic acid extraction method further includes: the fourth control valve is closed.

During specific implementation, after the step S200 and before the step S300, i.e., after the mixed liquid is moved into the extraction trough to mix with the magnetic bead and before controlling the flushing liquid accommodating cavity to introduce the flushing liquid into the extraction trough, the nucleic acid extraction method further includes the following steps.

A magnetic field is provided through the magnetic supply component to cause the magnetic bead to be adsorbed to the inner wall of the snake-shaped tube, and liquid that has reacted with the lysis solution and not bound to the magnetic bead is discharged through the second gas-pressure driven port; and the magnetic field is turned off through the magnetic supply component.

For a clearer understanding of the nucleic acid extraction method provided by the embodiments of the present disclosure, the following will be described in further detail with reference to the nucleic acid extraction microfluidic chip shown in FIG. 4A and FIG. 4B as an example.

Step one, the first control valve 191, the second control valve 192, the third control valve 193 and the fourth control valve 194 are controlled to be in an open state, i.e., all the control valves are initially open by default.

Step two, the sample liquid is injected through the sample inlet 160 into the mixed lysis groove 16; then, the sample inlet 160 is closed; the lysis solution accommodating cavity 32 is controlled to release the lysis solution; and the lysis solution is sucked into the mixed lysis groove 16 by applying negative pressure to the first gas-pressure driven port 131 to lyse the sample liquid by the lysis solution to form the mixed liquid. Specifically, by cycling positive and negative pressure, the sample liquid and the lysis solution are fully reacted for 10 minutes. Specifically, if heating is needed, the nucleic acid extraction device may further include: a first heating component disposed at a position corresponding to the mixed lysis groove 16, and specifically, the first heating component may be disposed on a side of the channel plate 1 away from the cover plate 2.

Step three, the mixed liquid is moved into the extraction trough 11 to mix with the magnetic bead 110 pre-coated in the extraction trough 11 by applying negative pressure to the first gas-pressure driven port 131 so as to allow the magnetic bead 110 to be bound to the nucleic acid formed by the sample liquid lysed, and specifically, the magnetic bead 110 and the nucleic acid may be in sufficient contact by positive and negative pressure cycles and left to stand for 1 minute.

Step four, the magnetic field is provided through the magnetic supply component to cause the magnetic bead 110 to be adsorbed to the inner wall of the extraction trough 11 (snake-shaped tube), and negative pressure is applied through the second gas-pressure driven port 132 to suck the liquid that has reacted with the lysis solution and has not been bound to the magnetic bead 110 into the waste liquid storage groove 18.

Step five, the magnetic field is turned off through the magnetic supply component.

Step six, the second control valve 192 is closed.

Step seven, the flushing solution accommodating cavity 31 is controlled to release the flushing liquid negative pressure is applied to the first gas-pressure driven port 131 to suck the flushing liquid into the extraction trough 11 for flushing for a first time period, the magnetic field is provided through the magnetic supply component to cause the magnetic bead 110 to be adsorbed to the inner wall of the extraction trough 11, and the liquid that has flushed the magnetic bead 110 is discharged into the waste liquid storage groove 18 through the second gas-pressure driven port 132; and the step is repeated at least one time.

Step eight, the first control valve 191 is closed.

Step nine, the magnetic field is turned off through the magnetic supply component, the eluent accommodating cavity 33 is controlled to release the eluent, and the eluent is sucked into the extraction trough 11 by applying negative pressure to the first gas-pressure driven port 131 so as to cause the eluent to react with the magnetic bead bound with the nucleic acid, so that the nucleic acid is separated from the magnetic bead 110. Specifically, if heating is needed, the nucleic acid extraction device may further include: a second heating component disposed at a position corresponding to the extraction trough 11, and the second heating component may be disposed on the side of the channel plate 1 away from the cover plate 2. Specifically, the first heating component and the second heating component may be structures independent from the nucleic acid extraction microfluidic chip, specifically may be disposed on an operation table on which the nucleic acid extraction is performed, and are disposed at a position corresponding to the nucleic acid extraction microfluidic chip when nucleic acid extraction is performed.

Step ten, the fourth control valve 194 is closed.

Step eleven, the magnetic field is provided by the magnetic supply component to cause the magnetic bead 110 to be adsorbed to the inner wall of the extraction trough 11 (snake-shaped tube), and negative pressure is applied to the first gas-pressure driven port 131 to suck an eluted nucleic acid solution into the sample storage groove 17.

Specifically, 50 μL of the lysis solution may be stored in the lysis solution accommodating cavity 32, 600 μL of the flushing liquid may be stored in the flushing liquid accommodating cavity 31, and 150 μl of an eluent may be stored in the eluent accommodating cavity 33. The magnetic bead 110 for extraction may be pre-coated in the extraction trough 11 (snake-shaped tube), and a supernatant mixed with the magnetic bead 110 may be sucked after the magnetic bead 110 is adsorbed by the magnetic supply component (e.g., a magnet) on the tube wall.

According to the nucleic acid extraction microfluidic chip provided by the embodiment of the present disclosure, the sample liquid is injected through the sample inlet of the cover plate into the mixed lysis zone, the lysis solution that can lyse the sample liquid is injected through the solution accommodating cavity into the mixed lysis zone, in the mixed lysis zone, the sample liquid is lysed by the lysis solution to obtain the nucleic acid by lysis, and thereafter, the mixed liquid obtained after lysis in the mixed lysis zone is moved into the extraction zone. In the extraction zone, the nucleic acid formed after lysis may be adsorbed by the magnetic bead and purified in a flushing mode by injection of the flushing liquid through the solution accommodating cavity. When the waste liquid that has flushed the magnetic bead is discharged, the magnetic field is applied externally to attract the magnetic bead in the region where the extraction zone is located so as to also attract the nucleic acid and discharge other liquids. The eluent is injected then through the solution accommodating cavity, and the eluent may separate the magnetic bead from the nucleic acid, effecting obtaining pure nucleic acid. In contrast to the device for obtaining nucleic acid in prior art, the nucleic acid extraction microfluidic chip provided by the embodiments of the disclosure may lower the risk that may arise from operator contact with exposed samples, the operation flow is simplified, a user does not need to provide an operation container himself, an entire extraction reaction can be completed in the microfluidic chip, errors that may arise from human operation are reduced, and portability is also improved.

While the preferred embodiments of the present disclosure have been described, further variations and modifications of these embodiments may be effected therein by those skilled in the art once the basic inventive concepts have come to mind. It is therefore intended that the appended claims be construed to include the preferred embodiments along with all changes and modifications that fall within the scope of the disclosure.

It will be apparent to those skilled in the art that various modifications and variations can be made to the embodiments of the present disclosure without departing from the spirit and scope of the embodiments of the present disclosure. Thus, it is intended that the present disclosure include such modifications and variations of the embodiments of the present disclosure provided they come within the scope of the present claims and their equivalents.

What is claimed is:

1. A nucleic acid extraction microfluidic chip, comprising:
   a channel plate, comprising:
      a first segment, a second segment, and a third segment arranged and connected sequentially in a first direction, wherein lengths in a second direction of the first segment, the second segment, and the third segment decrease sequentially, and the first segment comprises a first sub-segment and a second sub-segment protruding in the first direction relative to the second sub-segment, and a third sub-segment between the first sub-segment and the second sub-segment;
      a mixed lysis zone located in the second segment and the third segment, wherein the mixed lysis zone comprises:
         a first liquid inlet groove, a second liquid inlet groove, and a third liquid inlet groove;
         a first channel, a second channel, and a third channel communicating with the first liquid inlet groove, the second liquid inlet groove, and the third liquid inlet groove, respectively; and
         a mixed lysis groove, located at the second channel and communicating with the second channel;
      an extraction zone located in the third sub-segment, wherein the extraction zone comprises: an extraction trough with a liquid inlet end and a liquid outlet end, and the extraction trough communicates with the first channel, the second channel, and the third channel via the liquid inlet end;
      a first gas-pressure driven port located in the first sub-segment, wherein an end of the first gas-pressure driven port communicates with an exterior, and another end of the first gas-pressure driven port communicates with the extraction zone via a first sub-channel and the liquid outlet end; and
      a second gas-pressure driven port located in the second sub-segment, wherein an end of the second gas-pressure driven port communicates with the exterior, and another end of the second gas-pressure driven port communicates with the extraction zone via a second sub-channel and the liquid outlet end;
   a cover plate, disposed opposite to the channel plate, wherein the cover plate comprises:
      a sample inlet at a position corresponding to the mixed lysis groove; and
      a first liquid inlet through hole at a position corresponding to the first liquid inlet groove, a second liquid inlet through hole at a position corresponding to the second liquid inlet groove, and a third liquid inlet through hole at a position corresponding to the third liquid inlet groove; and
   a solution accommodating cavity, on a side of the cover plate away from the channel plate, wherein the solution accommodating cavity comprises:
      a flushing liquid accommodating cavity, in communication with the first liquid inlet groove of the channel plate through a first through hole;
      a lysis solution accommodating cavity, in communication with the second liquid inlet groove of the channel plate through a second through hole; and
      an eluent accommodating cavity, in communication with the third liquid inlet groove of the channel plate through a third through hole.

2. The nucleic acid extraction microfluidic chip according to claim 1, wherein the channel plate further comprises a sample storage groove at the first sub-channel; and
   the channel plate further comprises a waste liquid storage groove at the second sub-channel.

3. The nucleic acid extraction microfluidic chip according to claim 2, wherein the first channel, the second channel and the third channel converge at a liquid inlet channel to communicate with the liquid inlet end; and
   the waste liquid storage groove is further in communication with the liquid inlet channel through a fourth channel.

4. The nucleic acid extraction microfluidic chip according to claim 3, further comprising:

a magnetic bead positioned within the extraction trough; and a magnetic bead accommodating cavity on a side of the cover plate away from the channel plate;

wherein:

the mixed lysis zone further comprises a fourth liquid inlet groove, and a sixth-fifth channel communicating the fourth liquid inlet groove with the liquid inlet end;

the cover plate further comprises a fourth through hole corresponding to the fourth liquid inlet groove; and the magnetic bead accommodating cavity is in communication with the fourth liquid inlet groove of the channel plate through the fourth through hole.

5. The nucleic acid extraction microfluidic chip according to claim 2, further comprising:

a first control valve in the first channel;

a second control valve in the second channel;

a third control valve in the third channel; and a fourth control valve in the second sub-channel and between the waste liquid storage groove and the liquid outlet end.

6. The nucleic acid extraction microfluidic chip according to claim 5, wherein each of the control valves is a gas-pressure driven squeezing valve structure comprising: a squeezing block accommodating groove in a surface of the cover plate away from the channel plate, a squeezing block in the squeezing block accommodating groove, a bottom membrane on a side of the squeezing block away from the channel plate, and an elastic protective membrane on a side of the squeezing block facing the channel plate; wherein the bottom membrane comprises a gas circuit access port communicating with the squeezing block accommodating groove.

7. The nucleic acid extraction microfluidic chip according to claim 6, wherein a protective membrane accommodating groove accommodating the elastic protective membrane is provided in a surface of the cover plate, and an orthographic projection of the protective membrane accommodating groove on the cover plate covers an orthographic projection of the elastic protective membrane on the cover plate.

8. The nucleic acid extraction microfluidic chip according to claim 1, wherein the flushing liquid accommodating cavity and the eluent accommodating cavity are in a region where the third segment is located.

* * * * *